(12) United States Patent
Bejjani et al.

(10) Patent No.: US 7,425,413 B2
(45) Date of Patent: Sep. 16, 2008

(54) METHODS OF DESIGNING, SYNTHESIZING, AND PROPAGATING REFERENCE NUCLEIC ACIDS

(75) Inventors: Bassem A. Bejjani, Colbert, WA (US); Todd M. Christensen, Deer Park, WA (US)

(73) Assignee: Sacred Heart Medical Center, Spokane, WA (US)

( * ) Notice: Subject to any disclaimer, the term of this patent is extended or adjusted under 35 U.S.C. 154(b) by 0 days.

(21) Appl. No.: 10/731,419

(22) Filed: Dec. 9, 2003

(65) Prior Publication Data

US 2005/0202441 A1    Sep. 15, 2005

(51) Int. Cl.
*C12Q 1/68* (2006.01)
*C12P 19/34* (2006.01)

(52) U.S. Cl. .......................................... 435/6; 435/91.2

(58) Field of Classification Search ....................... None
See application file for complete search history.

(56) References Cited

U.S. PATENT DOCUMENTS

| | | | | |
|---|---|---|---|---|
| 5,759,822 | A * | 6/1998 | Chenchik et al. | 435/91.2 |
| 6,110,668 | A * | 8/2000 | Strizhov et al. | 435/6 |
| 6,607,911 | B2 * | 8/2003 | Gordon et al. | 435/320.1 |

FOREIGN PATENT DOCUMENTS

WO    WO03/078570    9/2003

OTHER PUBLICATIONS

Legay et al., Construction of an internal standard used in RT nested PCR for Borna Disease Virus RNA detection in biological samples. Vet. Res. (2000) 31: 565-572.*
Christensen, Todd M. et al., "Design, Development, Validation, and Use of Synthetic Nucleic Acid Controls for Diagnostic Purposes and Application to Cystic Fibrosis Testing", vol. 9, No. 3, Jul. 2007, pp. 315-319.
Loitsch, Stefan M. et al., "Reverse Transcription-Competitive Multiplex PCT Improves Quantification of mRNA in Clinical Samples-Application to the Low Abundance CFTR mRNA", vol. 45, No. 5, May 1999, pp. 619-624.
European Search Report for Application No. 04813464.7, mailed Feb. 5, 2008 (7 pages).
PCT Notification of Transmittal of the International Search Report, Jun. 7, 2006.
PCT Written Opinion Of the International Searching Authority, Jun. 7, 2006.

* cited by examiner

*Primary Examiner*—Kenneth R. Horlick
*Assistant Examiner*—David C Thomas
(74) *Attorney, Agent, or Firm*—Lee & Hayes, PLLC

(57) ABSTRACT

Subject matter includes design, synthesis, and propagation of synthetic and semi-synthetic reference nucleic acids and mixtures of reference nucleic acids for use in genetic tests, such as molecular screening, mutation testing, carrier testing, and diagnostic assays. In one implementation, methods are described for design, synthesis, and propagation of reference nucleic acid mixtures and a system is presented for using the mixtures.

17 Claims, 15 Drawing Sheets

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Example Synthetic Sequence

<400> SEQUENCE: 1
agctattcgc tagccgaaat agcgg                                           25

<210> SEQ ID NO 2
<211> LENGTH: 16
<212> TYPE: DNA
<213> ORGANISM: Artificial Sequence
<220> FEATURE:
<223> OTHER INFORMATION: Example Synthetic Sequence

<400> SEQUENCE: 2
ctggccgtcg ttttac                                                    16

<210> SEQ ID NO 3
<211> LENGTH: 17
<212> TYPE: DNA
<213> ORGANISM: Artificial Sequence
<220> FEATURE:
<223> OTHER INFORMATION: Example Synthetic Sequence

<400> SEQUENCE: 3
caggaaacag ctatgac                                                   17

<210> SEQ ID NO 4
<211> LENGTH: 16
<212> TYPE: DNA
<213> ORGANISM: Artificial Sequence
<220> FEATURE:
<223> OTHER INFORMATION: Example Synthetic Sequence

<400> SEQUENCE: 4
gaccggcagc aaaatg                                                    16

<210> SEQ ID NO 5
<211> LENGTH: 17
<212> TYPE: DNA
<213> ORGANISM: Artificial Sequence
```

```
<220> FEATURE:
<223> OTHER INFORMATION: Example Synthetic Sequence

<400> SEQUENCE: 5
caggaaacag ctatgac                                                         17

<210> SEQ ID NO 6
<211> LENGTH: 42
<212> TYPE: DNA
<213> ORGANISM: Artificial Sequence
<220> FEATURE:
<223> OTHER INFORMATION: Example Synthetic Sequence

<400> SEQUENCE: 6
gtcctttgtc gatactgtcg ataagcgatc ggctttatcg cc                             42

<210> SEQ ID NO 7
<211> LENGTH: 41
<212> TYPE: DNA
<213> ORGANISM: Artificial Sequence
<220> FEATURE:
<223> OTHER INFORMATION: Example Synthetic Sequence

<400> SEQUENCE: 7
tcgataagcg atcggcttta tcgccgaccg gcagcaaaat g                              41

<210> SEQ ID NO 8
<211> LENGTH: 17
<212> TYPE: DNA
<213> ORGANISM: Artificial Sequence
<220> FEATURE:
<223> OTHER INFORMATION: Example Synthetic Sequence

<400> SEQUENCE: 8
gtcctttgtc gatactg                                                         17

<210> SEQ ID NO 9
<211> LENGTH: 37
<212> TYPE: DNA
<213> ORGANISM: Artificial Sequence
<220> FEATURE:
<223> OTHER INFORMATION: Example Synthetic Sequence

<400> SEQUENCE: 9
caggaaacag ctatgacagc tattcgctag ccgaaat                                   37

<210> SEQ ID NO 10
<211> LENGTH: 9
<212> TYPE: DNA
<213> ORGANISM: Artificial Sequence
<220> FEATURE:
<223> OTHER INFORMATION: Example Synthetic Sequence

<400> SEQUENCE: 10 tgatgatga                                                                   9

<210> SEQ ID NO 11
<211> LENGTH: 8
<212> TYPE: DNA
<213> ORGANISM: Artificial Sequence
<220> FEATURE:
<223> OTHER INFORMATION: Example Synthetic Sequence

<400> SEQUENCE: 11 ccggaatt                                                                    8
```

```
<210> SEQ ID NO 12
<211> LENGTH: 13
<212> TYPE: DNA
<213> ORGANISM: Artificial Sequence
<220> FEATURE:
<223> OTHER INFORMATION: Example Synthetic Sequence

<400> SEQUENCE: 12
agattcgcta gcc                                                          13

<210> SEQ ID NO 13
<211> LENGTH: 13
<212> TYPE: DNA
<213> ORGANISM: Artificial Sequence
<220> FEATURE:
<223> OTHER INFORMATION: Example Synthetic Sequence

<400> SEQUENCE: 13
gaaatcgtag cgg                                                          13

<210> SEQ ID NO 14
<211> LENGTH: 12
<212> TYPE: DNA
<213> ORGANISM: Artificial Sequence
<220> FEATURE:
<223> OTHER INFORMATION: Example Synthetic Sequence

<400> SEQUENCE: 14
gatcggcttt ag                                                           12

<210> SEQ ID NO 15
<211> LENGTH: 26
<212> TYPE: DNA
<213> ORGANISM: Artificial Sequence
<220> FEATURE:
<223> OTHER INFORMATION: Example Synthetic Sequence

<400> SEQUENCE: 15
agattcgcta gccgaaatcg tagcgg                                            26

<210> SEQ ID NO 16
<211> LENGTH: 6
<212> TYPE: DNA
<213> ORGANISM: Artificial Sequence
<220> FEATURE:
<223> OTHER INFORMATION: Example Synthetic Sequence

<400> SEQUENCE: 16 ctttag                                                                   6

<210> SEQ ID NO 17
<211> LENGTH: 59
<212> TYPE: DNA
<213> ORGANISM: Artificial Sequence
<220> FEATURE:
<223> OTHER INFORMATION: Example Synthetic Sequence

<400> SEQUENCE: 17
gtcctttgtc gatactgaga ttcgctagcc ctttagcatc gccgaccggc agcaaaatg        59

<210> SEQ ID NO 18
<211> LENGTH: 59
<212> TYPE: DNA
<213> ORGANISM: Artificial Sequence
<220> FEATURE:
<223> OTHER INFORMATION: Example Synthetic Sequence
```

-continued

```
<400> SEQUENCE: 18
caggaaacag ctatgactct aagcgatcgg gaaatcgtag cggctggccg tcgttttac          59
```

METHODS OF DESIGNING, SYNTHESIZING, AND PROPAGATING REFERENCE NUCLEIC ACIDS

SEQUENCE LISTING

A sequence listing in accordance with 37 CFR 1.822 and WIPO Standard ST.25 and produced by PATENTIN software version 3.3 is provided beginning on a separate sheet, on four sheets of paper and incorporated by reference into the specification. A sequence listing identical to the paper version is provided in duplicate in computer readable form (CRF) on two CDs, each containing a single file "SH1-0001US.ST25.TXT" of size 3.87 kilobytes that is incorporated by reference into the specification and is an exact duplicate of the sequence listing provided on paper. The file SH1-0001US.ST25.TXT is compatible with IBM-PC, MS-DOS, and MS-Windows applications.

TECHNICAL FIELD

The subject matter relates generally to molecular biology and more specifically to methods of designing, synthesizing and propagating reference nucleic acids.

BACKGROUND

Medical diagnostic tests in clinical laboratories commonly require stringent quality control as mandated by government agencies and standards organizations. The National Committee for Clinical Laboratory Standards (NCCLS) suggests accreditation guidelines that include calibrating equipment against control samples and performing tests of patient samples in tandem with consistent references (NCCLS, Villanova, Pa.). Other organizations, such as the Joint Commission on Accreditation of Healthcare Organizations (JCAHO) and the American Society for Clinical Pathology (ASCP) also recommend or mandate standardized clinical procedures often requiring updated (non-expired) and well-inventoried supplies of clinical reference reagents and controls (JCAHO, Washington D.C.; ASCP, Chicago, Ill.). Control references must be tested in conjunction with each test of a patient sample according to the Clinical Laboratory Improvement Act of 1988, which applies to over 175,000 laboratory entities (CLIA '88 is described at 42 C.F.R., parts 493.1-493.1850). The College of American Pathologists (CAP) and the American College of Medical Genetics (ACMG) also mandate comparison with references during each patient test (CAP, Northfield, Ill.; ACMG, Bethesda, Md.).

Clinical assays often involve either deoxyribonucleic acid (DNA) or ribonucleic acid (RNA). For example, nucleic acid diagnostics may be performed to find infectious DNA or RNA from an invading virus or bacteria. Reference nucleic acids are typically used as chromatographic, spectroscopic, and/or spectrophotometric controls, for example during gel electrophoresis monitored by a laser "electric eye."

DNA provides a template for generating bodily proteins using sequences of four DNA bases (adenine, thymine, guanine, and cytosine). The mutation of any one base in a single-stranded DNA sequence may be enough to form a defective allele resulting in disease. Many disease moieties thus have an underlying genetic etiology.

A gene is a length of DNA on a chromosome associated with some particular process or characteristic of an individual. A gene is conventionally considered a fundamental building block of heredity that determines observable characteristics, i.e., the "phenotype" of the individual organism. The underlying "chemical" genetic constitution of the individual is instead called its "genotype."

Genes are observed to be lined up on human chromosomes in a sequential order. The sequential order of genes is the same for both members of a chromosome pair. Therefore genes occur in pairs (homologous genes). The two genes in a pair may occur in different forms called "alleles" and the phenotypic expression of one allele or the other in a pair depends on the types of alleles present. Mutations are the changes in the DNA sequence that may convert one allele to another. An individual who carries two of the same alleles is homozygous for that gene while an individual who has two different alleles for a gene pair is heterozygous for that gene. The occurrence of mutations that are deleterious to the normal expression of an allele may result in malfunction of that allele. The co-occurrence of a "normal" allele with a "mutated" (or abnormal) allele at the same gene in a heterozygous individual may result in a new (or disease) phenotype. In such a case, the mutated allele is described as acting in a dominant fashion over the normal allele. If the mutated allele does not cause any change in phenotype of the heterozygous individual, but causes a change (or disease) only when the individual is homozygous for that mutated allele, the mutated allele is described as acting in a recessive fashion compared to the normal allele. Thus, dominance and recessiveness describe the relative effect of gene expression of an allele when two distinct alleles occur together.

Carriers of genetic diseases typically carry a heterozygous recessive allele that includes a mutation capable of causing the disease. However, the mutated recessive allele may not be expressed in the carrier because its deleterious effect on the phenotype is masked by the normal (non-mutated) allele. Thus, a carrier may possess mutations in his genotype that can be passed down to descendents to cause the disease yet the carrier presents a normal phenotype (expressed characteristics) and is thus disease free. On the other hand, a person who experiences a genetically mediated disease may be a heterozygous "carrier" who has a mutated dominant allele for the disease. Still further, a person who experiences a disease may be a homozygous "carrier" with identical homologous genes that each has a mutation at a particular locus that causes the disease.

Given the number of different kinds of genetic diseases, the different possibilities for homozygous and heterozygous causation, and the need for both disease and carrier testing, maintaining recommended or mandated clinical supplies of high quality nucleic acid references and controls (hereinafter referred to as "reference nucleic acids" or just "references") presents daunting challenges to genetics reference facilities and molecular diagnostic laboratories. As shown in FIG. 1, a reference nucleic acid 100 to be amplified for use as a test control comprises single-stranded or double-stranded reference RNA or DNA of known quantity and known quality within currently accepted tolerances. The ideal reference nucleic acid 100 to be amplified should resemble the patient sample to be tested as closely as possible and moreover, should be usable in all configurations of a given type of test. However, a reference nucleic acid 100 for clinical use may not be easily available in an adequate quantity and quality. Further, once an adequate quantity and quality of the reference nucleic acid 100 is obtained, the reference also needs to be reasonably easy to manufacture and store. These various requirements are difficult to meet because a single patient test often includes many diverse steps, such as polymerase chain reactions, enzymatic manipulations, sequencing reactions, hybridizations, electrophoreses, etc., each placing a different demand on the reference. Limited sources for obtaining a reference nucleic acid 100 to be amplified exacerbate a quality problem by causing a short supply leading to an increased likelihood that references of lower quality will be allowed in order to bolster the supply.

Typically, a reference nucleic acid 100 to be amplified originates from a human source 102, but if not available in sufficient quantity or not amenable to storage, then conventional chemical synthesis 104 may augment or replace the human source 102. Depending on the identity of the reference nucleic acid 100 to be amplified and its origin, various methods may be needed to refine, develop and increase the supply, each method yielding a product that may or may not have consistent quality with products yielded by other methods. A first conventional method 106 may merely isolate and purify the reference nucleic acid 100 to be amplified from a human source 102 and/or from conventional chemical synthesis 104. A second conventional method 108 may replicate the reference nucleic acid 100 to be amplified by cloning in a vector (e.g., a plasmid) and allowing a species of bacteria to propagate the vector. A third conventional method 110 may undertake amplification of a human-derived reference nucleic acid 100 in an automated cycler. Other conventional methods not reviewed here are represented by an "Nth" conventional method 112 that yields a variable, heterogeneous product. Most of these known methods yield products that may have inconsistent quality and/or stability, and many of the example methods are cumbersome and expensive, as well as dependent on starting materials from a human source 102.

SUMMARY

Subject matter includes design, synthesis, and propagation of synthetic and semi-synthetic reference nucleic acids and mixtures of reference nucleic acids for use in tests, such as molecular screening, genetic testing, carrier testing, and diagnostic assays. In one implementation, methods are described for design, synthesis, and propagation of reference nucleic acid mixtures and a system is presented for using the mixtures.

DETAILED DESCRIPTION

Overview

Figure 1:
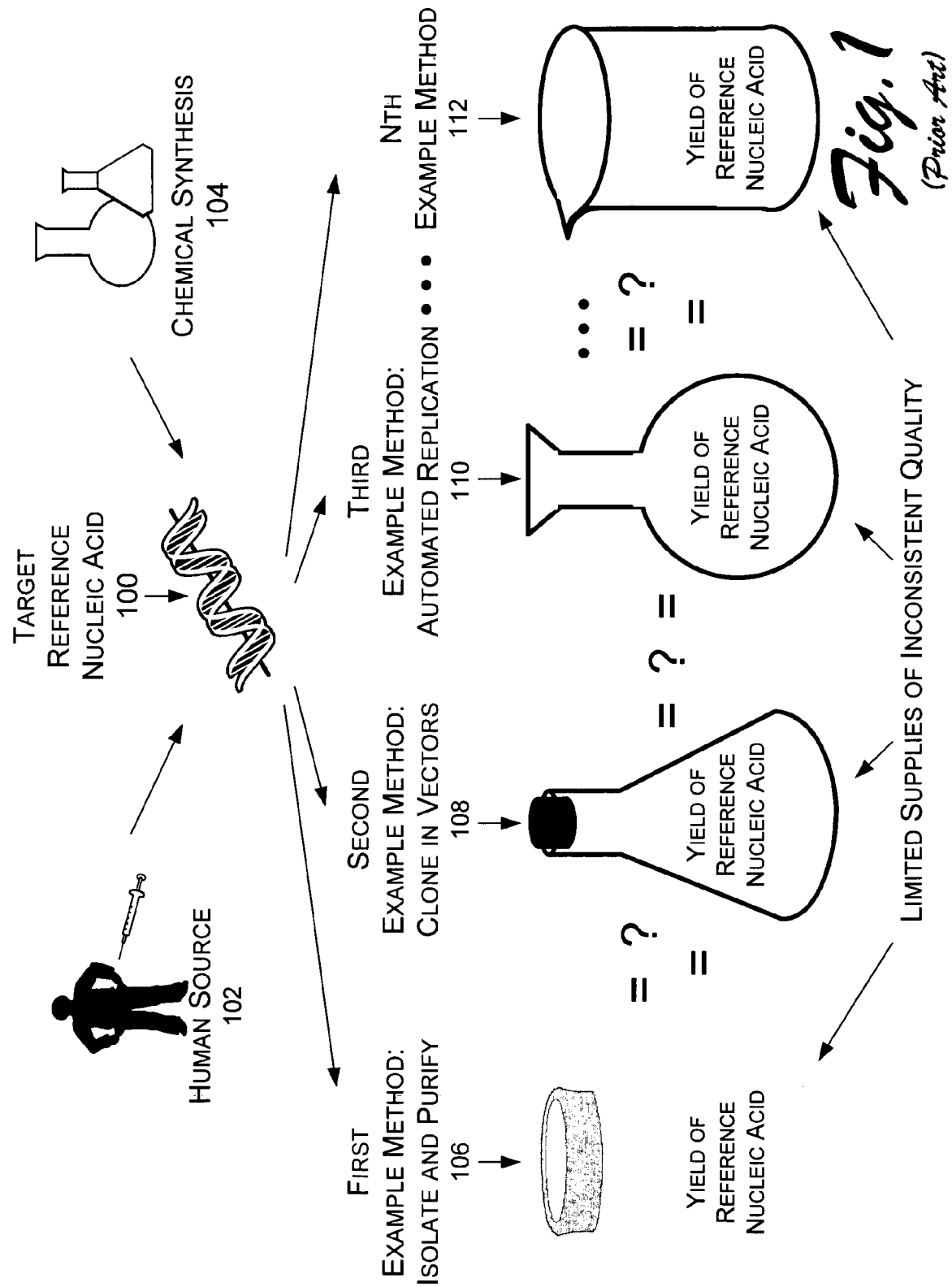
FIG. 1 is a graphic representation of conventional methods of obtaining nucleic acids.

The subject matter describes methods of designing, synthesizing and/or propagating synthetic nucleic acid sequences for use as references in molecular diagnostic and genetic testing—especially mutation testing—of human or nonhuman nucleic acids. In one aspect of the subject matter, relatively short segments of much larger genomic nucleic acids are designed, synthesized, and amplified because they have relevance as clinical references or controls—thus eliminating conventional problems associated with conventionally producing many irrelevant segments of large nucleic acids in quantity along with the few relevant segments. Because the segments that have relevance as clinical references are often relatively short, the subject matter includes synthesis of reference nucleic acids and mixtures thereof that are relatively easy to design and synthesize and capable of being manipulated to advantage during amplification, other enzymatic modification, and detection.

In one implementation, for example, the subject matter can be used to amplify an entire mixture of reference nucleic acids in concert. In another or the same implementation, the subject matter can be used to build a large, clinically relevant, nucleic acid polynucleotide in easy-to-synthesize smaller segments. These implementations, singly or in combination, allow the production of nucleic acids and nucleic acid mixtures that may be otherwise unobtainable or may be obtainable at a lower quality and at greater effort and expense by conventional methods.

Amplifying an entire mixture of reference nucleic acids in concert has multiple uses. For example, in many genetic diseases, any one of several hundred mutations in a single gene may cause the disease. The several hundred mutations do not occur together in a real gene that exists in nature. The subject matter presented here, however, can create a single nucleic acid mixture that models, for purposes of mutation testing, all of multiple mutations as if a hypothetical gene or DNA segment having all the multiple mutations were present.

An exemplary synthesis of a reference nucleic acid mixture to be amplified ("amplified" and "propagated" are used somewhat interchangeably herein) first includes synthesizing the starting constituents to be used as "seed templates" for producing a desired reference nucleic acid mixture. In one implementation, the constituents may include a collection of polymeric or oligomeric nucleic acid sequences of interest, for example, a collection of oligonucleotides each representing a mutated section of a gene or of any DNA segment. In another or the same implementation, the constituents of the reference nucleic acid mixture are segments of a larger polynucleotide to be assembled into the larger polynucleotide by exemplary methods presented below with respect to FIGS. 11 and 12. The subject matter that will be described below allows the designing practitioner to produce relatively complex mixtures and/or relatively complex molecules while only having to perform multiple syntheses of relatively short and simple sequences.

The production of a complex reference nucleic acid mixture and/or the assemblage of one or more large molecules can be executed via an exemplary system of "tags:" nucleic acid sequences for priming, bridging, and/or overlapping the constituent reference nucleic acids. For example, during the synthesis of each constituent reference nucleic acid a first nucleic acid tag is bound to (e.g., synthesized onto) a first end of the particular reference nucleic acid. The first tag provides a priming site for the first of two primers for an amplification procedure. The synthesis further includes binding (e.g., synthesizing) a second tag to a second end of the reference nucleic acid to be amplified. The second tag provides a template for the first primer to create a priming site for the second primer on a complementary nucleic acid strand produced by the first primer. In other words, the first tag has a base sequence that complements a base sequence of the first primer while the second tag has the same base sequence as the second primer. In each of a series of polymerase chain reaction (PCR) amplifications, the first primer is extended into single-stranded complements of the original tagged reference nucleic acid (100 in FIG. 4) while the second primer is extended into copies of the original tagged reference nucleic acid using the single-stranded complements produced by the first primer as templates.

Thus, an exemplary method includes synthesizing multiple single-stranded reference nucleic acids and tagging each of the multiple reference nucleic acids with a copy of the above-described first nucleic acid tag and a copy of the second nucleic acid tag, i.e., on opposite and appropriate ends of each of the multiple reference nucleic acids. When the mixture of reference nucleic acids is exposed to the first and second primers in one or more PCR amplifications, the entire mixture is amplified using only the two primers. Because in this example each of the multiple reference nucleic acids, including tags, can be "human designed" and because propagation of the entire mixture is by one primer set, a high degree of process control is available to an architect of reference nucleic acids and a high degree of quality and reproducibility is afforded to the resulting reference nucleic acid mixture.

As mentioned above, amplifying an exemplary reference nucleic acid mixture is useful in many kinds of tests. For example, in mutation testing requiring a different nucleic acid control reagent for testing each of multiple gene mutations that could be responsible for a disease, exemplary subject matter allows the multiple control reagents to be combined into one mixture and amplified indefinitely into a supply that has consistent quality and consistent proportion of constituent reference nucleic acids.

Exemplary Methods

Figure 2:
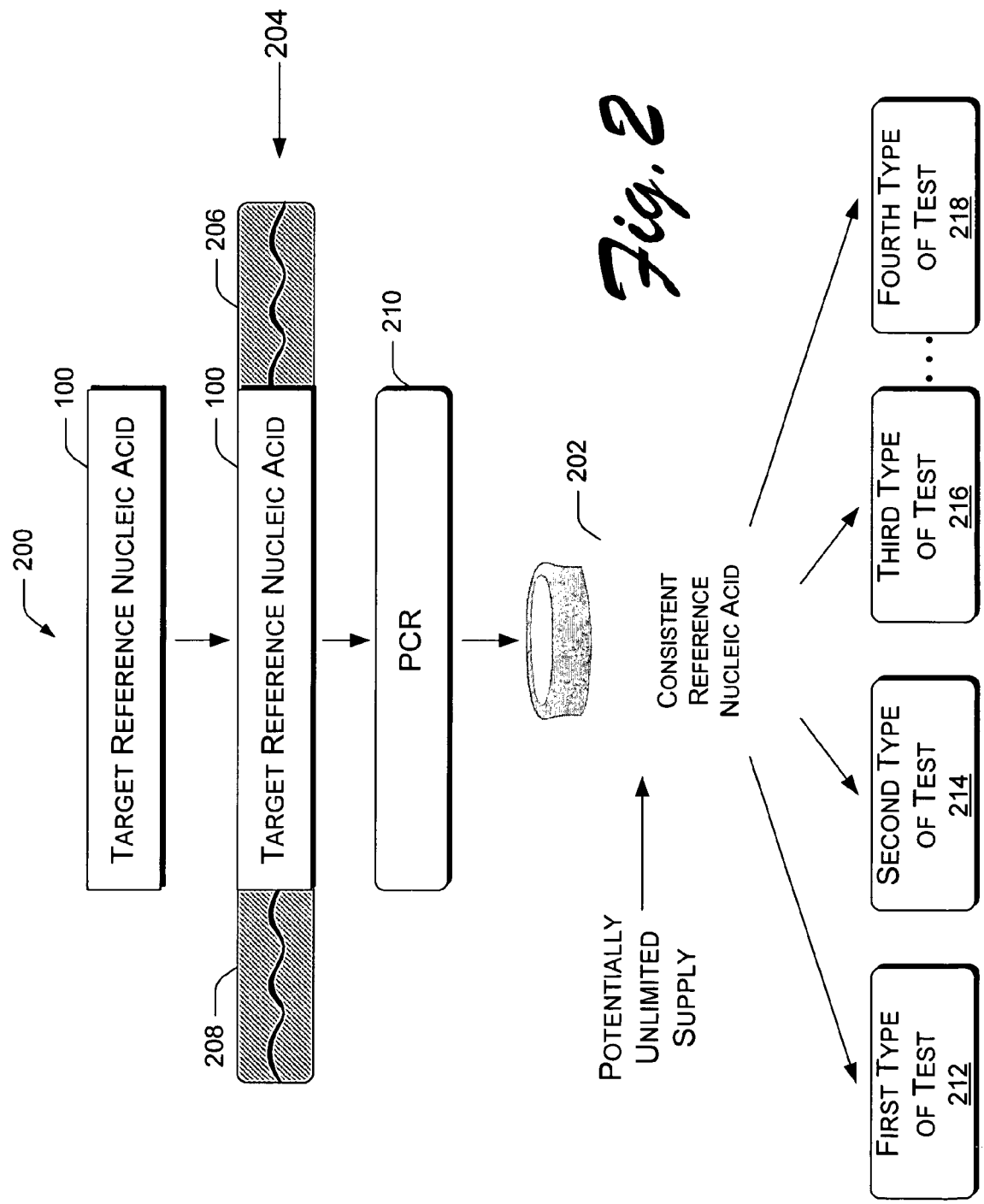
FIG. 2 is a graphic representation of an exemplary method of producing a reference nucleic acid.

FIG. 2 shows an exemplary method 200 of producing a consistent and potentially unlimited supply 202 of a reference nucleic acid. In one implementation, the exemplary method 200 includes synthesizing a tagged target reference nucleic acid 204 to be amplified. The (untagged) reference nucleic acid 100 to be amplified, of course, has a base sequence capable of being used at least in part as a clinical reference. The exemplary method 200 includes synthesizing a first exemplary tag 206 on one end of the reference nucleic acid 100 to be amplified, for example, oriented for "forward" sequence extension, and a second exemplary tag 208 on the opposing end of the reference nucleic acid 100 to be amplified, for example, oriented for "reverse" sequence extension of a complementary strand. In one implementation, the first exemplary tag 206 has a base sequence complementary to a base sequence of a first primer of a primer set and the second exemplary tag 208 has the same base sequence as a second primer of the primer set. The first tag 206 anneals to one of the primers (or vice versa depending on viewpoint) and the resulting primed strand becomes a template for producing its complement strand through extension of the first primer. The second tag 208 anneals to no primer, but provides a template for making a priming site on the complementary strand. Thus the complementary strand includes a complement of the second tag 208, which anneals to the second primer. The primed complement strand becomes a template for producing a copy of the original nucleic acid strand by extension of the second primer. Both the original tagged reference nucleic acid 204 and its complementary strand can be amplified at the same time during PCR cycles.

A potentially unlimited supply of a consistently reproducible reference nucleic acid 202 can thus be obtained for use in a myriad of clinical tests (e.g., 212, 214, 216, . . . , 218) where the easy availability of supply and the reproducibility of the reference nucleic acids are desirable as features for a standard to be used for comparing results between different types of clinical tests.

Figure 3:
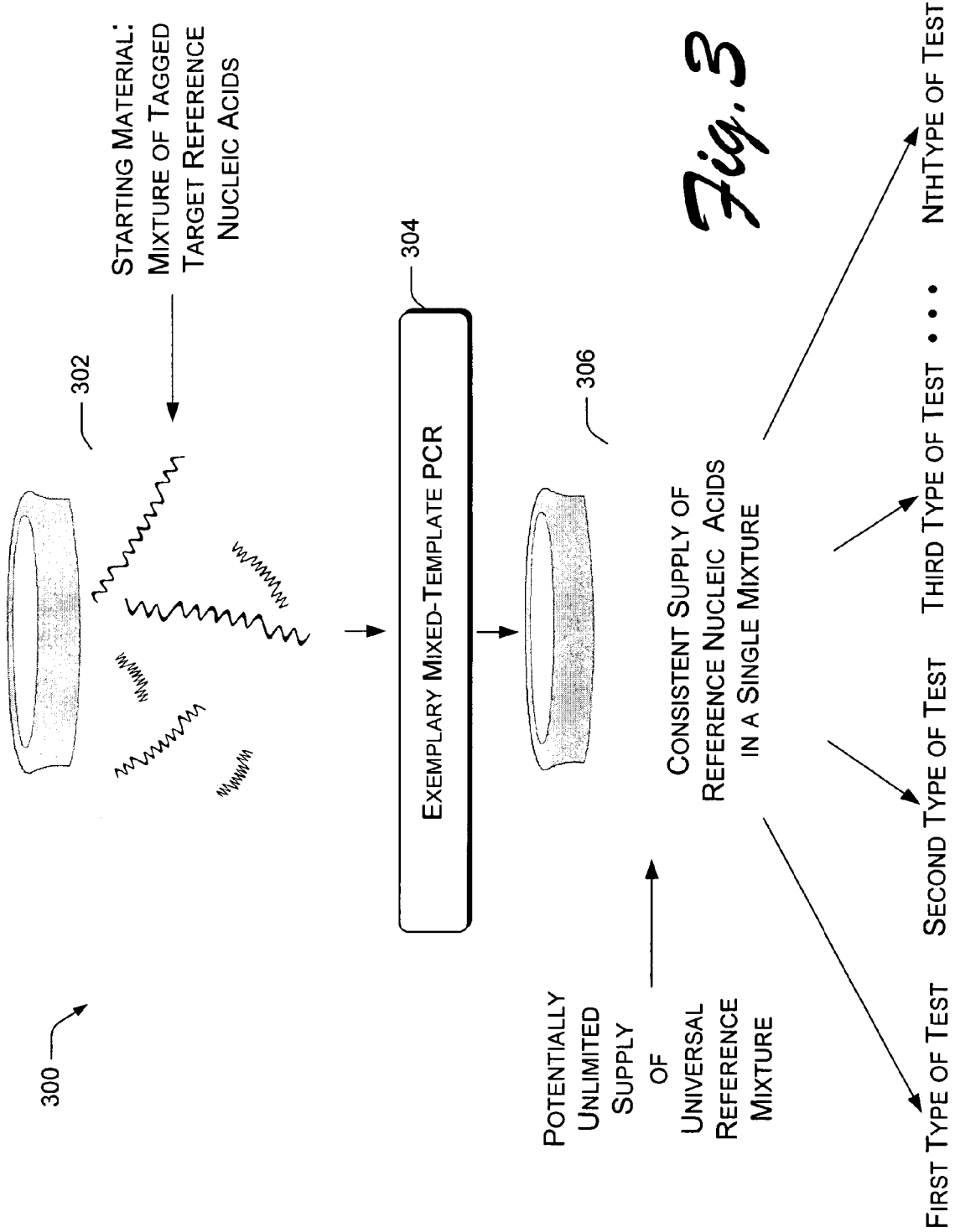
FIG. 3 is a graphic representation of an exemplary method of producing a mixture of reference nucleic acids.

FIG. 3 shows another exemplary method 300 according to another aspect of the subject matter. A starting mixture 302 includes multiple reference nucleic acid constituents each tagged with copies of the same exemplary first and second nucleic acid tags (e.g., 206, 208 in FIG. 2). The starting mixture 302 undergoes a PCR process, such as an exemplary mixed-template PCR 304, to yield a supply of consistently reproducible reference nucleic acids in a single mixture 306.

When the starting mixture 302 includes constituent reference nucleic acids that are oligonucleotides or polynucleotides each synthesized to represent a different standard reference, then the exemplary method 300 produces a single mixture 306 that can be used as a single universal reference for many different types of tests, that is, as a multiplexed assay or universal reference, at least with respect to tests compatible with the particular type of constituent reference nucleic acids in the single mixture 306 being produced (in other words, the universality of a single mixture 306 may be limited by the reagent characteristics specifically required by specific conventional machines or other conventional apparatuses). An exemplary system for utilizing reference nucleic acids in a single mixture 306 is discussed below with respect to FIG. 11.

An exemplary supply of reference nucleic acids in a single mixture 306 may replace multiple separate conventional nucleic acid references. For example, cystic fibrosis is a disease that may be caused by the mutation of a single base pair in any one of several hundred different sites on the cystic fibrosis transmembrane conductance regulator (CFTR) gene. Testing for 30-33 of the commonest of these mutations—using 30-33 different nucleic acid reference "controls"—can provide a successful diagnosis for over 90% of cystic fibrosis cases in Caucasian populations. Instead of requiring the conventional 30-33 different nucleic acid references in 30-33 different containers (or cumbersome mixtures thereof), an exemplary method 300 using the subject matter produces a supply of reference nucleic acids in a single mixture 306 for all 30-33 tests: the single mixture 306 is amplified as a mixture. This exemplary method can be scaled to produce a supply of much more than just 30-33 different nucleic acid references in a single mixture 306.

Exemplary Synthetic Reference Nucleic Acids

Figure 4:
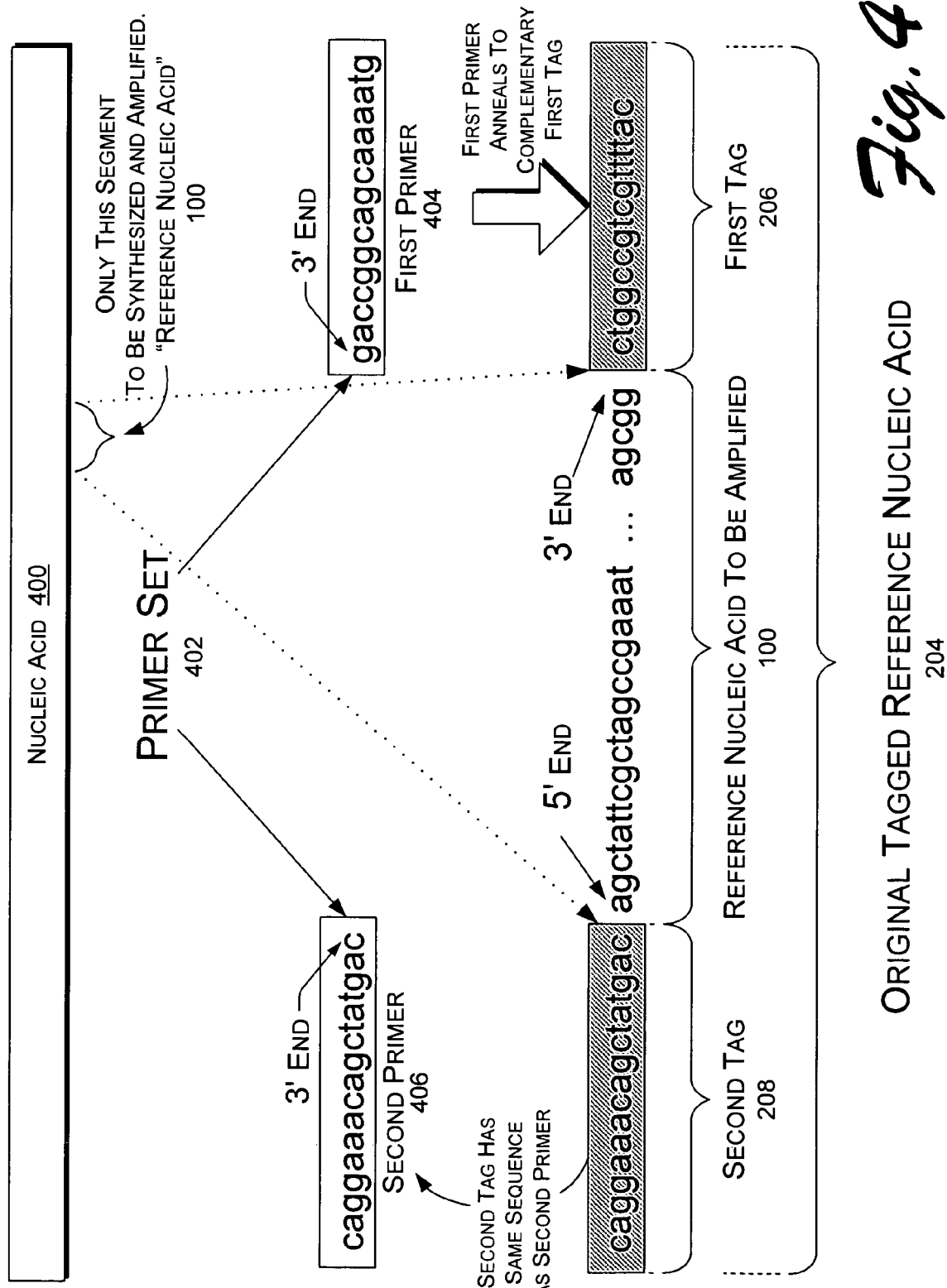
FIG. 4 is a graphic representation of an example synthetic reference nucleic acid of SEQ ID NO: 1 tagged with example first tag SEQ ID NO: 2 and example second tag SEQ ID NO: 3, and example primer set consisting of example first primer SEQ ID NO: 4 and example second primer SEQ ID NO: 5.

FIG. 4 shows, in greater detail than in FIG. 2, an original tagged reference nucleic acid 204 (SEQ ID NO: 1 plus SEQ ID NO: 2 plus SEQ ID NO: 3) to be used as a starting template in a PCR process. The (untagged) reference nucleic acid 100 SEQ ID NO: 1 to be amplified is typically a segment of a larger nucleic acid polynucleotide, such as a genomic nucleic acid 400 that has a base sequence at least a part of which is used as a clinical reference or as a building block for a clinical reference. The base sequence and length of the illustrated reference nucleic acid 100 SEQ ID NO: 1 to be amplified is merely an example for description purposes. Actual examples of oligonucleotides and/or polynucleotides to be amplified may be different in sequence and length than those illustrated. Likewise, the first primer 404 SEQ ID NO: 4 and second primer 406 SEQ ID NO: 5 are depicted as a universal M13 forward primer (that has seventeen bases) and a universal M13 reverse primer (that has sixteen bases), respectively, only for the sake of example. Other primers may be used or designed, such as any one of an M13 phage vector sequence or primer, Lambda, SP6, T3, or T7 primers, or any arbitrarily designed base sequence present in nature or completely invented by the architect, depending on, or independent of the reference nucleic acid 100 SEQ ID NO: 1 to be amplified.

In one implementation, the base sequence of each tag (206, 208—SEQ ID NO: 2 and SEQ ID NO: 3) is typically designed to be unique so that the bases in the tags do not pair with a span of the bases in the reference nucleic acid 100 SEQ ID NO: 1 to be amplified (or complementary strands thereof). Using tags (206, 208—SEQ ID NO: 2 and SEQ ID NO: 3) with unique base sequences prevents formation of unwanted artifacts, such as secondary nucleic acid structures, duplexes, concatemers, etc. Each tag is bound to its oligonucleotide in an orientation that allows an associated primer to extend copies of the original strand and complementary strands.

In another implementation, more than one pair of tags may be synthesized to allow more flexibility for manipulating a specific nucleic acid sequence or set of sequences in a complex mixture of sequences. The multiple pairs of tags may be attached to selected reference nucleic acid species in the mixture to provide differential propagation and control of the different selections. Hence, it is possible to orchestrate propagation of very complex reference nucleic acid mixtures having precise proportions of the constituents, e.g., by varying multiple primer and/or target nucleic acid concentrations.

In the illustrated implementation, the first tag 206 SEQ ID NO: 2 has a base sequence complementary to a first primer 404 SEQ ID NO: 4 of a primer set 402. The complementariness between the first tag 206 SEQ ID NO: 2 and the first primer 404 SEQ ID NO: 4 allows the first primer 404 SEQ ID NO: 4 to anneal to the original tagged reference nucleic acid 204 (SEQ ID NO: 1 plus SEQ ID NO: 2 plus SEQ ID NO: 3) and extend (that is, be extended by a polymerase) in the 3' direction—new bases are added by the polymerase on to the 3' end of the primer.

The second tag 208 SEQ ID NO: 3 has a base sequence that matches (i.e., is the same as) a base sequence of a second primer 406 SEQ ID NO: 5 of the primer set 402. The second primer 406 SEQ ID NO: 5 does not anneal to the original tagged reference nucleic acid 204 since its sequence is the same as the second tag 208 SEQ ID NO: 3 segment of the original tagged reference nucleic acid 204, but anneals to a complementary priming site (506 in FIG. 5—SEQ ID NO: 8) created on a complementary nucleic acid strand by extension of the first primer 404 SEQ ID NO: 4, for example, in a previous PCR cycle. Hence, on an original tagged reference nucleic acid 204, the first tag 206 SEQ ID NO: 2 acts as a priming site while the second tag 208 SEQ ID NO: 3 creates a priming site on the strand complementary to the original tagged reference nucleic acid 204.

Figure 5:
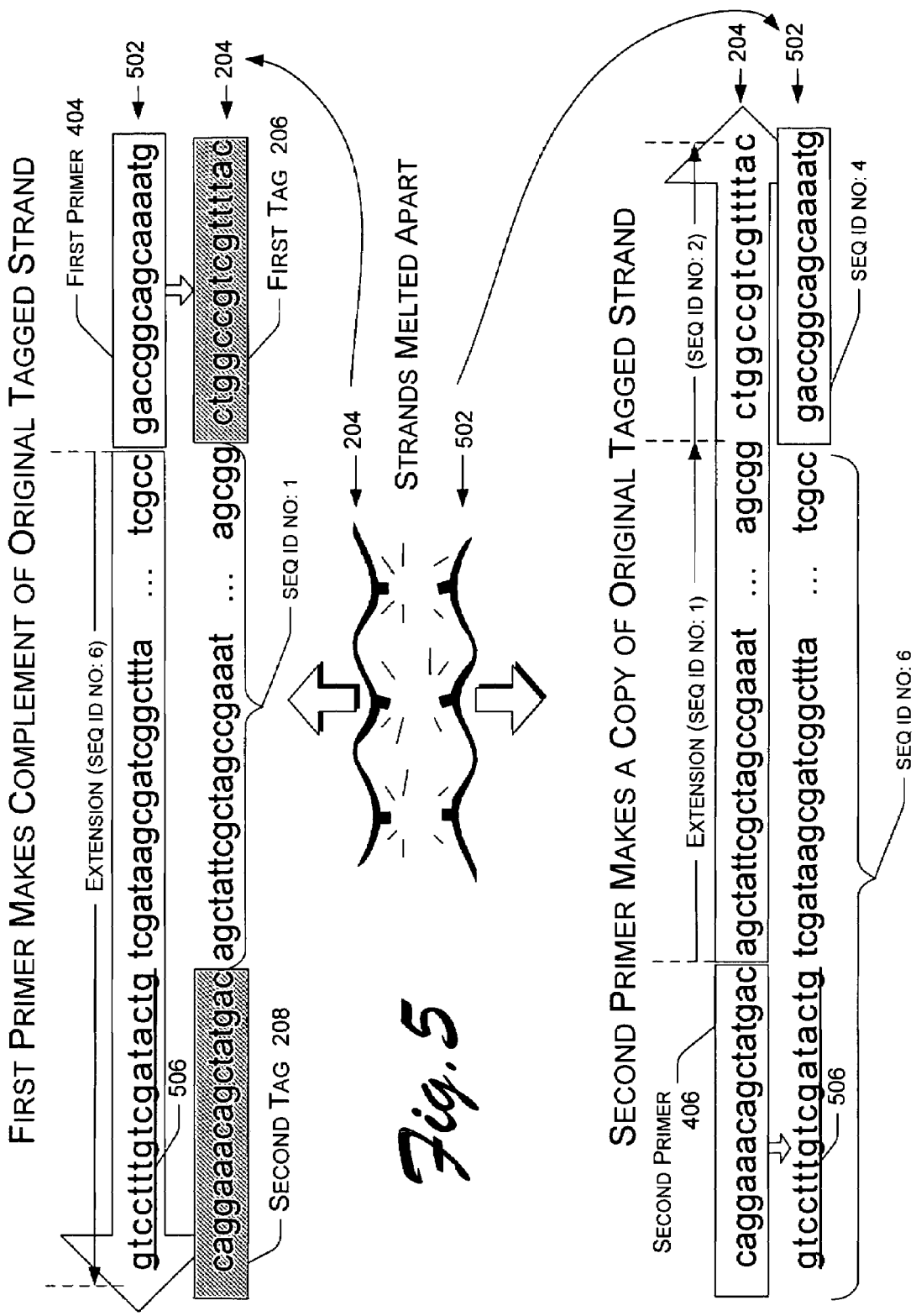
FIG. 5 is a graphic representation of a polymerase chain reaction cycle using an example synthetic reference nucleic acid SEQ ID NO: 1 tagged with example first tag SEQ ID NO: 2 and example second tag SEQ ID NO: 3, wherein an example first primer SEQ ID NO: 4 makes complementary strand SEQ ID NO: 6 and example second primer SEQ ID NO: 5 makes copy strand SEQ ID NO: 1 plus SEQ ID NO: 2.

FIG. 5 shows an exemplary reference nucleic acid production method 500 according to the subject matter in which a first primer 404 SEQ ID NO: 4 priming a synthetic tagged reference nucleic acid 204 (SEQ ID NO: 1 plus SEQ ID NO: 2 plus SEQ ID NO: 3) is extended into a complementary strand 502 (SEQ ID NO: 4 plus SEQ ID NO: 6) of the original synthetic tagged reference nucleic acid 204, thus forming a duplex (204 bound to 502). The complementary strand 502 includes a priming site 506 SEQ ID NO: 8 that is complementary to the second tag 208 SEQ ID NO: 3. After the duplex undergoes denaturation, a second primer 406 SEQ ID NO: 5 priming the complementary strand 502 is extended into a copy of the original tagged reference nucleic acid 204. The amplification of the original tagged reference nucleic acid 204 and its complement 502 continues through multiple PCR cycles using, in one implementation, exemplary PCR components and reaction parameters, such as those indicated in Appendix A: "Synthetic Control Design Parameters: Exemplary PCR Components and Reaction Parameters," incorporated herein by reference. The duplex is denatured as per known PCR methods to separate the strands (204, 502) of the duplex. In the annealing and extension parts of subsequent PCR cycles, the second primer 406 SEQ ID NO: 5 makes further copies of the original tagged reference nucleic acid 204 while the first primer 404 SEQ ID NO: 4 makes further copies of complementary strands of the original tagged reference nucleic acid 204. The PCR cycles of denaturation, annealing, extension, and denaturation are repeated, e.g., approximately thirty times, to produce millions of copies of the original tagged reference nucleic acid 204 having the reference base sequence for clinical use and millions of copies of its complementary strand 502.

Figure 6:
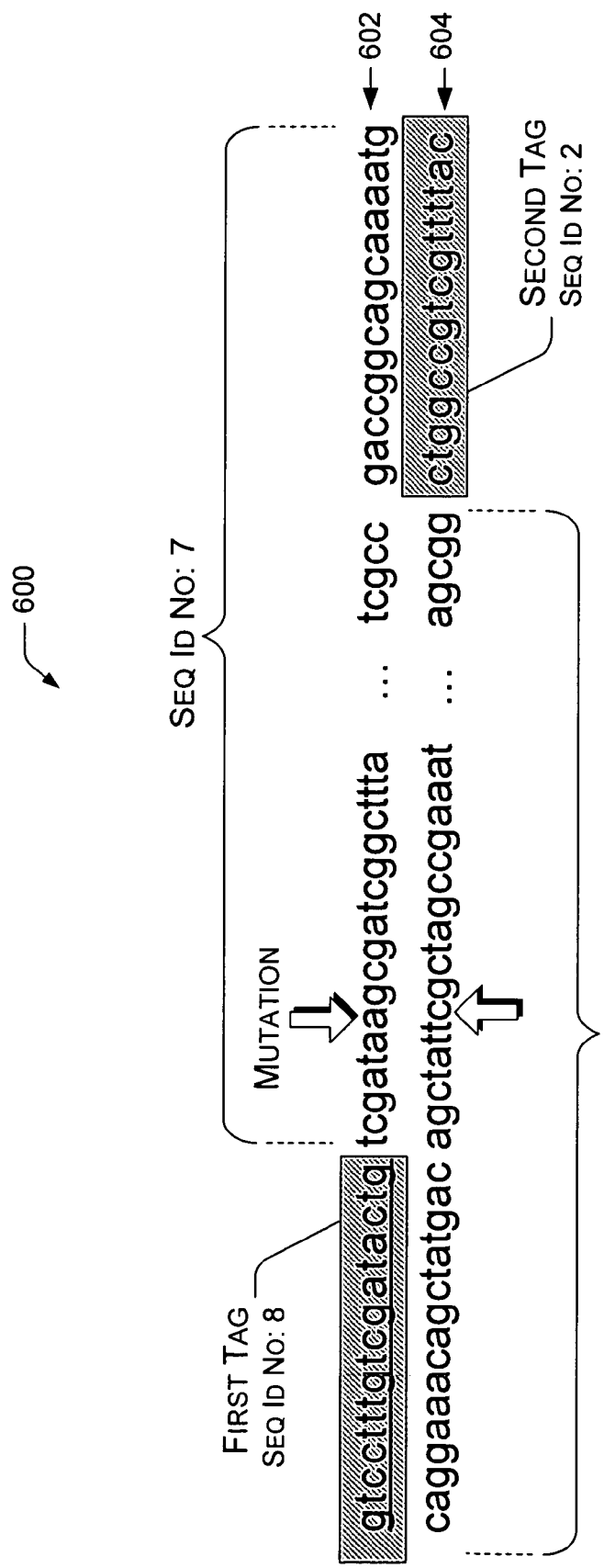
FIG. 6 is a graphic representation of an exemplary synthetic tagged duplex of a reference nucleic acid, synthesized as an example first sequence SEQ ID NO: 7 with an example first tag SEQ ID NO: 8 and an example second sequence SEQ ID NO: 9 with an example second tag SEQ ID NO: 2.

FIG. 6 shows an exemplary synthetic reference nucleic acid synthesized as a duplex 600, that is, as two complementary nucleic acid oligonucleotides 602 (SEQ ID NO: 7 plus SEQ ID NO: 8), and 604 (SEQ ID NO: 9 plus SEQ ID NO: 2), or, polynucleotides each having one exemplary tag on one end). This provides an alternative exemplary method for synthesizing reference nucleic acids that include or do not include mutations, using one or more of the exemplary tags described with respect to FIGS. 4 and 5. Hence, a single-stranded reference nucleic acid can be synthesized to include a tag on each end (FIGS. 4 and 5), which thereafter relies on PCR reagents and reactions to produce complements, or two complementary strands, each having one tag, can be synthesized from the outset (as in FIG. 6).

Exemplary Mixtures of Synthetic Reference Nucleic Acids

Figure 7:
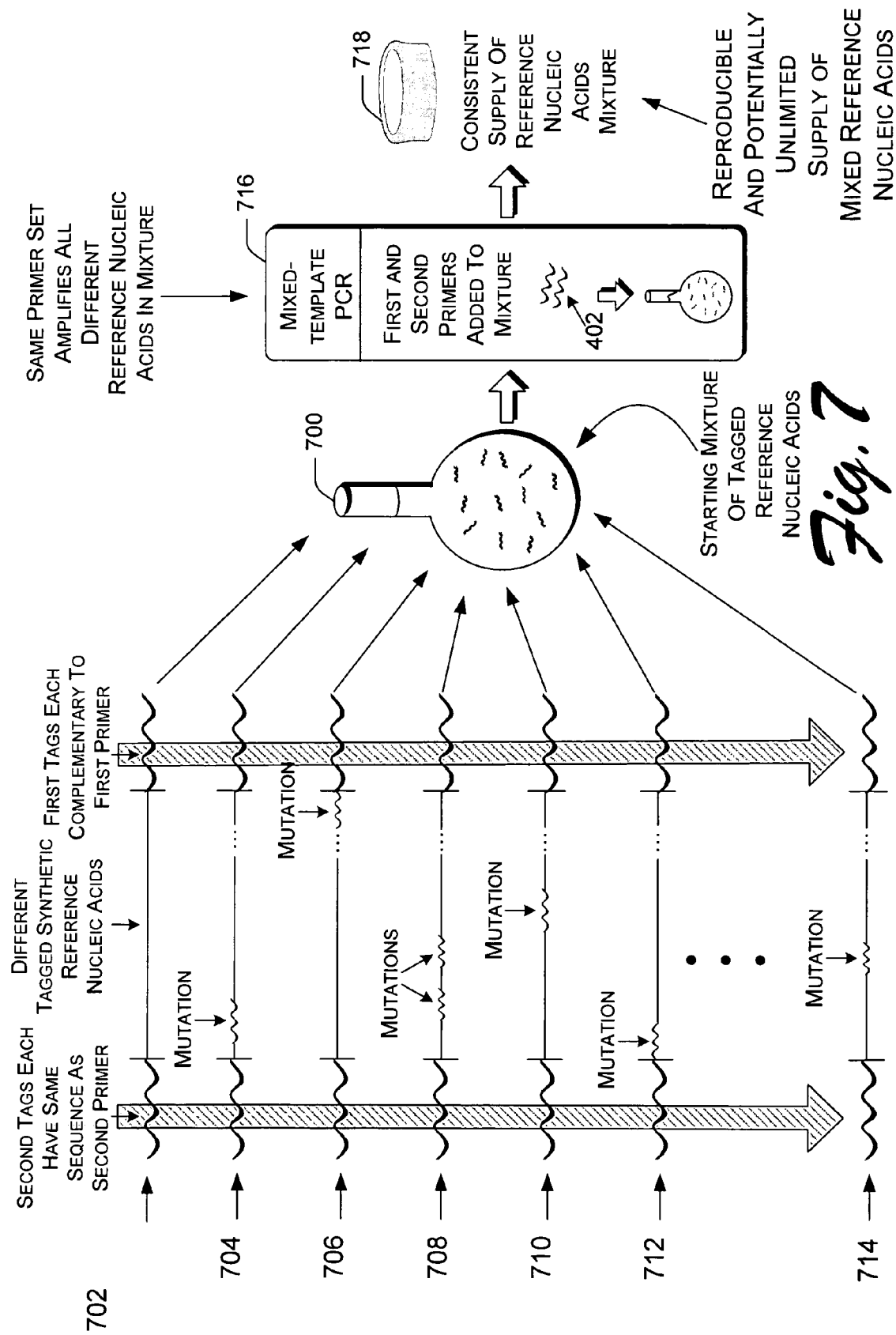
FIG. 7 is a graphic representation of production of an exemplary mixture of reference nucleic acids.

FIG. 7 shows an exemplary mixture 701 of tagged reference nucleic acids (702, 704, 706, 708, 710, 712, . . . , 714) that may be used as a starting material for a PCR amplification process to obtain a potentially unlimited, reproducible, and consistent supply of reference nucleic acid mixture 718. Copies of a first nucleic acid tag 206 are bound to a first end of each of the multiple reference nucleic acids, wherein each copy of the first nucleic acid tag 206 has a base sequence complementary to a base sequence of a first primer 404 of a primer set 402. Copies of a second nucleic acid tag 208 are bound to a second end of each of the multiple reference nucleic acids, wherein each copy of the second nucleic acid tag 208 has a base sequence matching a base sequence of a second primer 406 of the primer set 402.

During an exemplary mixed-template PCR 716, a single primer set 402 is added to the exemplary mixture 701 of tagged reference nucleic acids. The exemplary mixed-template PCR 716 produces a supply of reference nucleic acids mixture 718 that can be reproduced consistently in potentially unlimited quantity.

In one implementation, the tagged reference nucleic acids (702, 704, 706, 708, 710, 712, . . . , 714) are each synthesized to represent at least one mutation in a base sequence of a gene, for example, the CFTR gene. The different tagged reference nucleic acids (702, 704, 706, 708, 710, 712, . . . , 714) are designed and synthesized, when possible, to have similar lengths if such similarity facilitates uniform amplification.

Table 1 below is a list of known common mutations of the CFTR gene causing cystic fibrosis (Cystic Fibrosis Genetic Analysis Consortium (1994)). Although the subject matter can be used with respect to many different types of genetic testing, cystic fibrosis mutation testing is used as an illustrative disease. One example of a consistent supply of a reference nucleic acid mixture 718 that is designed, synthesized, and propagated according to the subject matter includes a tagged reference nucleic acid for each CFTR gene mutation listed below in Table 1, that is, for each mutation listed in Table 1 a tagged reference nucleic acid is synthesized with a base sequence that includes at least one, and possibly more than one of the known mutation:

TABLE 1

| Name of Mutation |
| --- |
| [[Delta]]F508 |
| G542X |
| G551D |
| N1303K |
| W1282X |
| R553X |
| 621 + 1G->T |
| 1717 – 1G->A |
| R117H |
| R1162X |
| R347P |
| 3849 + 10kbC->T |
| [[Delta]]I507 |
| 394delTT |
| G85E |
| R560T |
| A455E |
| 1078delT |
| 2789 + 5G->A |
| 3659delC |
| R334W |
| 1898 + 1G->T |
| 711 + 1G->T |
| 2183AA->G |
| 3905insT |

TABLE 1-continued

| Name of Mutation |
| --- |
| S549N |
| 2184delA |
| Q359K/T360K |
| M1101K |
| Y122X |
| 1898 + 5G->T |
| 3120 + 1G->A |
| I148T |

Of course, other exemplary supplies of reference nucleic acid mixtures 718 designed, synthesized, and/or propagated according to the subject matter may have different constituent tagged reference nucleic acids comprising more CFTR gene mutations or fewer CFTR gene mutations than those shown in Table 1. Still other exemplary supplies of reference nucleic acids mixtures 718 designed, synthesized, and/or propagated according to the subject matter may have different tagged reference nucleic acids used in tests for other genetic conditions and circumstances unrelated to cystic fibrosis.

Figure 8:
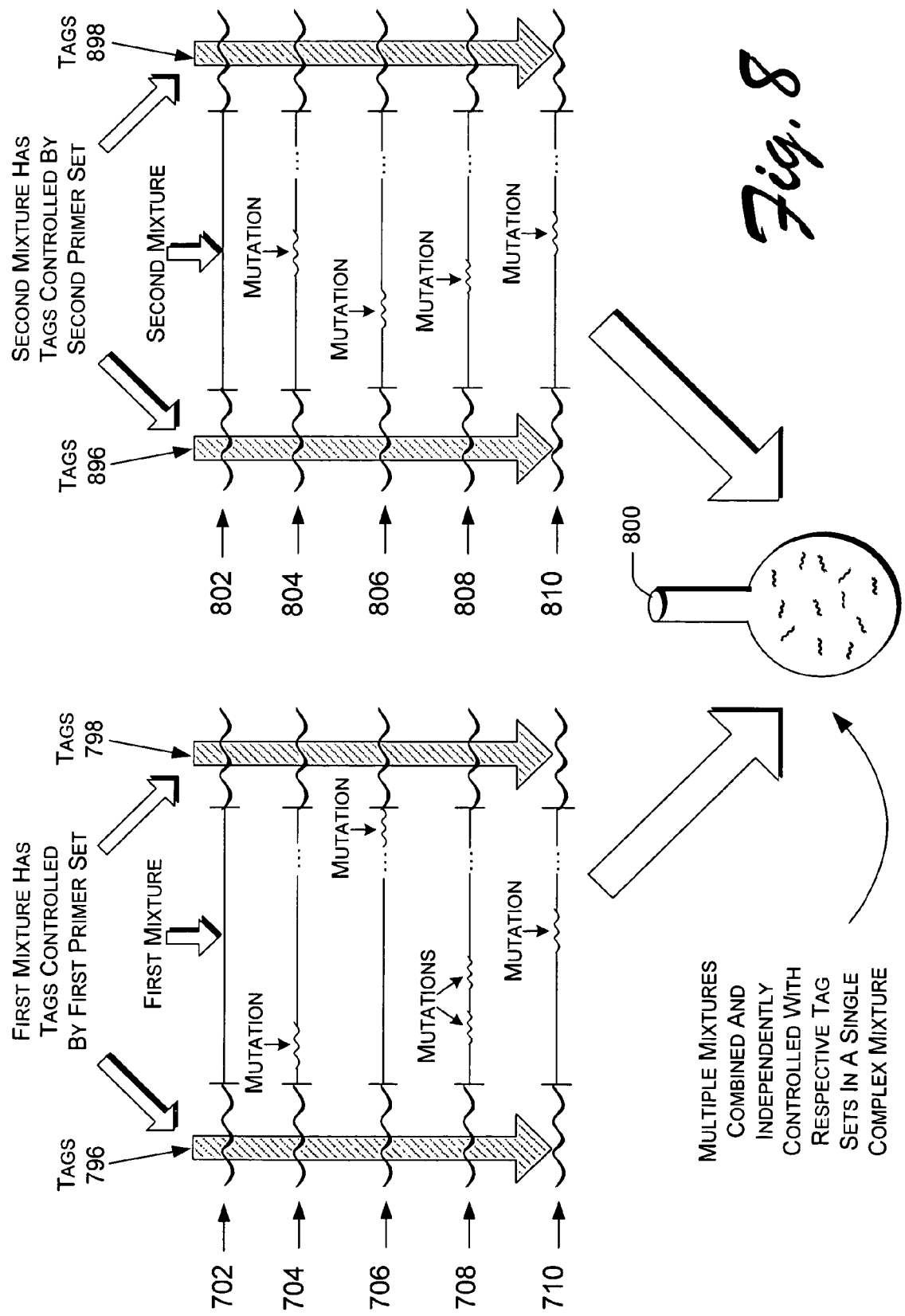
FIG. 8 is a graphic representation of an exemplary mixture of multiple mixtures, wherein the propagation of each of the multiple mixtures is controlled by an associated primer set.

FIG. 8 shows an exemplary complex mixture 800 (also known as "master mixture") of reference nucleic acid sequences 800, i.e., a "mixture of mixtures" in which more than one pair of tags may be synthesized to allow more flexibility for manipulating a specific nucleic acid sequence or set of sequences in the complex mixture 800. As mentioned, the multiple pairs of tags may be attached to selected reference nucleic acid species in the mixture to provide differential propagation and control of the different selections. Hence, it is possible to orchestrate propagation of very complex reference nucleic acid mixtures having precise proportions of the constituents, e.g., by varying multiple primer concentrations and/or by strategically attaching various tag sets to predetermined reference nucleic acid sequences.

In one implementation, each member of a first mixture of diverse reference nucleic acids (702, 704, 706, 708, 710) may be flanked by copies of the same set of tags 796, 798 and may be controlled accordingly via a primer set tuned to the tags 796, 798 (e.g., M13 tuned tags). Each member of a second mixture of diverse reference nucleic acids (802, 804, 806, 808, 810) may be flanked by copies of a different set of tags 896, 898 (e.g., T3/T7 tuned tags) and may be controlled accordingly via a second primer set tuned to the tags 896, 898. The process of selecting different tags to control different mixtures within one "master" mixture 800 may be extended to multiple mixtures and/or multiple individual species within the master mixture 800.

In the same or another implementation, by adding specific amounts of the primers that are specific for tagged sequences that require special treatment the level of amplification and other enzymatic manipulation can be finely adjusted. Hence, if a reference nucleic acid sequence "X" is particularly difficult to visualize in a detection assay, it may be desirable to have ten times more of sequence X than any other. Sequence X can be tagged with unique tags (e.g., TX1 and TX2) whereas other nonremarkable reference nucleic acid sequences, A, B, C, . . . Z are all tagged with the same tags (e.g., TA1 and TA2), but different tags than used for sequence X. This provides more control over manipulating sequence X than for controlled the other sequences in the complex mixture 800.

Figure 9:
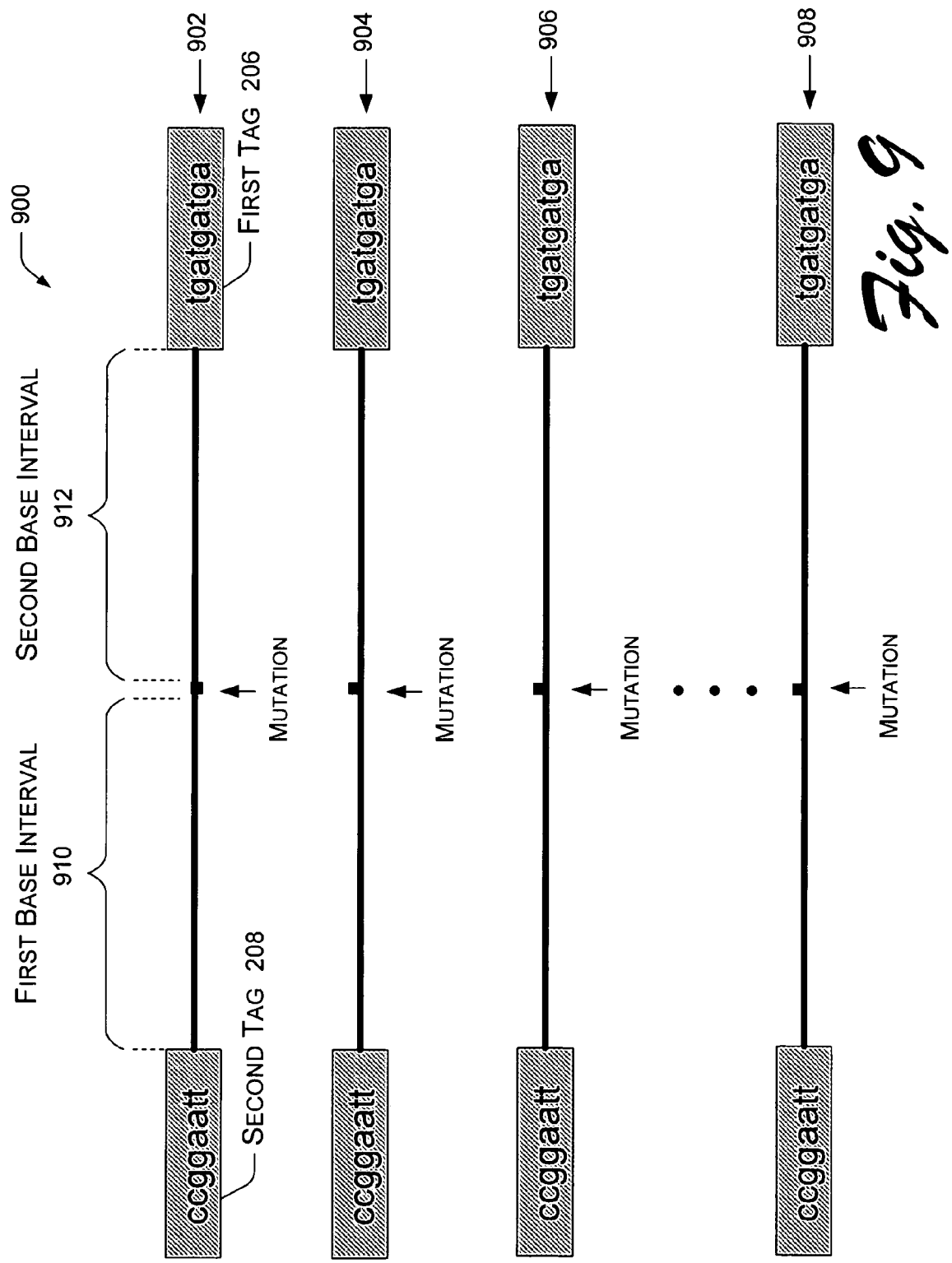
FIG. 9 is a graphic representation of exemplary base sequence intervals providing isolation of reference mutation sequences from example tags SEQ ID NO: 10 and SEQ ID NO: 11, thereby facilitating production of multiple reference nucleic acids representing genetic mutations.

FIG. 9 shows an exemplary reference nucleic acid mixture 900, wherein each constituent reference nucleic acid (902, 904, 906, 908) embodies additional design features for producing a mixture product of consistent and reproducible quality. Each single mutation represented in each different reference nucleic acid may be surrounded by base intervals 910, 912 of similar length, that is, each mutation site can be surrounded on both sides by approximately the same number of bases between the site of a mutation and each nucleic acid tag 206 SEQ ID NO: 10 and 208 SEQ ID NO: 11. This "padding" of roughly uniform length between a mutation site and tags on a given reference nucleic acid distances the mutation site from possible interference with PCR processes, other subsequent enzymatic manipulation, and other processes involving the tags 206 SEQ ID NO: 10 and 208 SEQ ID NO: 11. The base intervals 910, 912 around a mutation site can be synthesized using the same base sequence arrangements as are present at corresponding sites of a normal model gene on which the mutation occurs, if such a gene exists, or can be synthesized as arbitrary sequences. In one implementation, the similarly-sized base intervals 910, 912 on either side of one or more mutations may add up to a span of between approximately forty and approximately sixty bases, resulting in total polynucleotide lengths that provides a good value given synthesis costs. In other implementations, the base intervals 910, 912 on either side of one or more mutation sites may add up to spans of approximately eighty, one hundred, or even more than one hundred bases.

Figure 10:
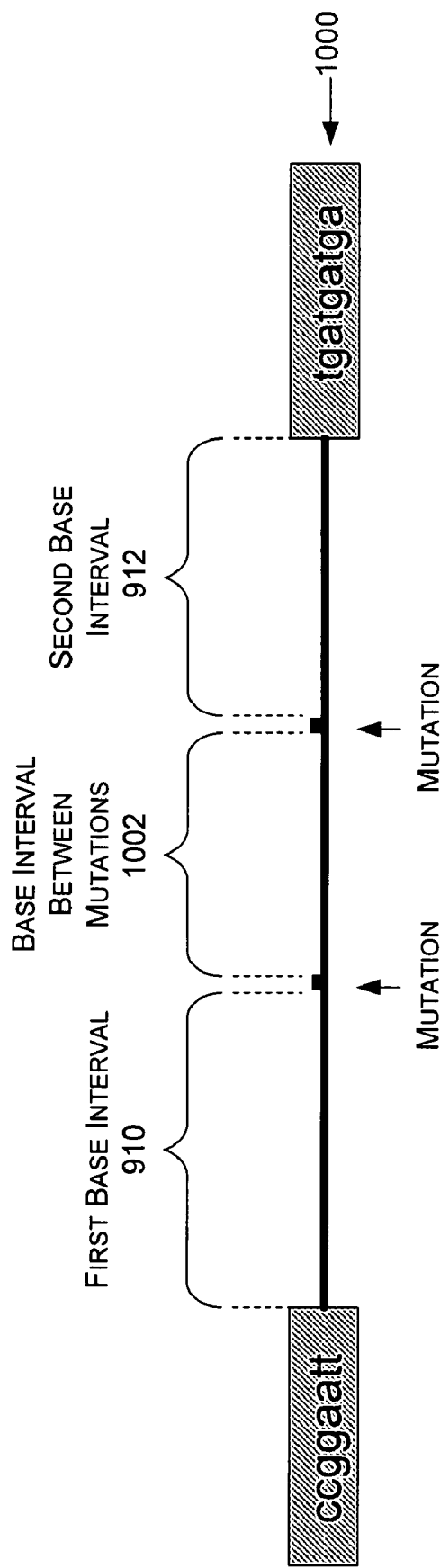
FIG. 10 is a graphic representation of exemplary base intervals providing isolation of multiple reference mutation sequences from each other and from example tags SEQ ID NO: 10 and SEQ ID NO: 11, thereby facilitating production of an exemplary reference nucleic acid representing multiple genetic mutations.

Likewise, as shown in FIG. 10, if two or more mutations are present in an exemplary reference nucleic acid 1000 with tags on each end (SEQ ID NO: 10 and SEQ ID NO: 11), substantially uniform base intervals 910, 912, 1002 may be designed into the reference nucleic acid 1000 to separate the two mutations. Thus, design geometry for optimizing PCR amplification and subsequent manipulation of the PCR product in light of multiple different references being present in a mixture can be implemented in each of multiple reference nucleic acids in a mixture, as exemplified by the illustrated reference nucleic acid 1000. Design considerations for references to be used in a mixture of references can include those that prevent steric impediments to PCR amplification and subsequent manipulation of the PCR product, such as avoiding a variety of significantly different sized reference nucleic acids as starting templates and avoiding tag designs that might lead to secondary structure artifacts in a mixture of references.

Since each constituent reference nucleic acid (e.g., 1000) to be used as an original tagged reference nucleic acid 204 in a mixture can be synthesized de novo by the subject matter, problem configurations can be designed out of references. The resulting consistent reference nucleic acid supply (e.g., 718) can therefore achieve superior quality, reproducibility and consistency over conventional methods.

Exemplary Reference Nucleic Acid Extension Methods

Figure 11:
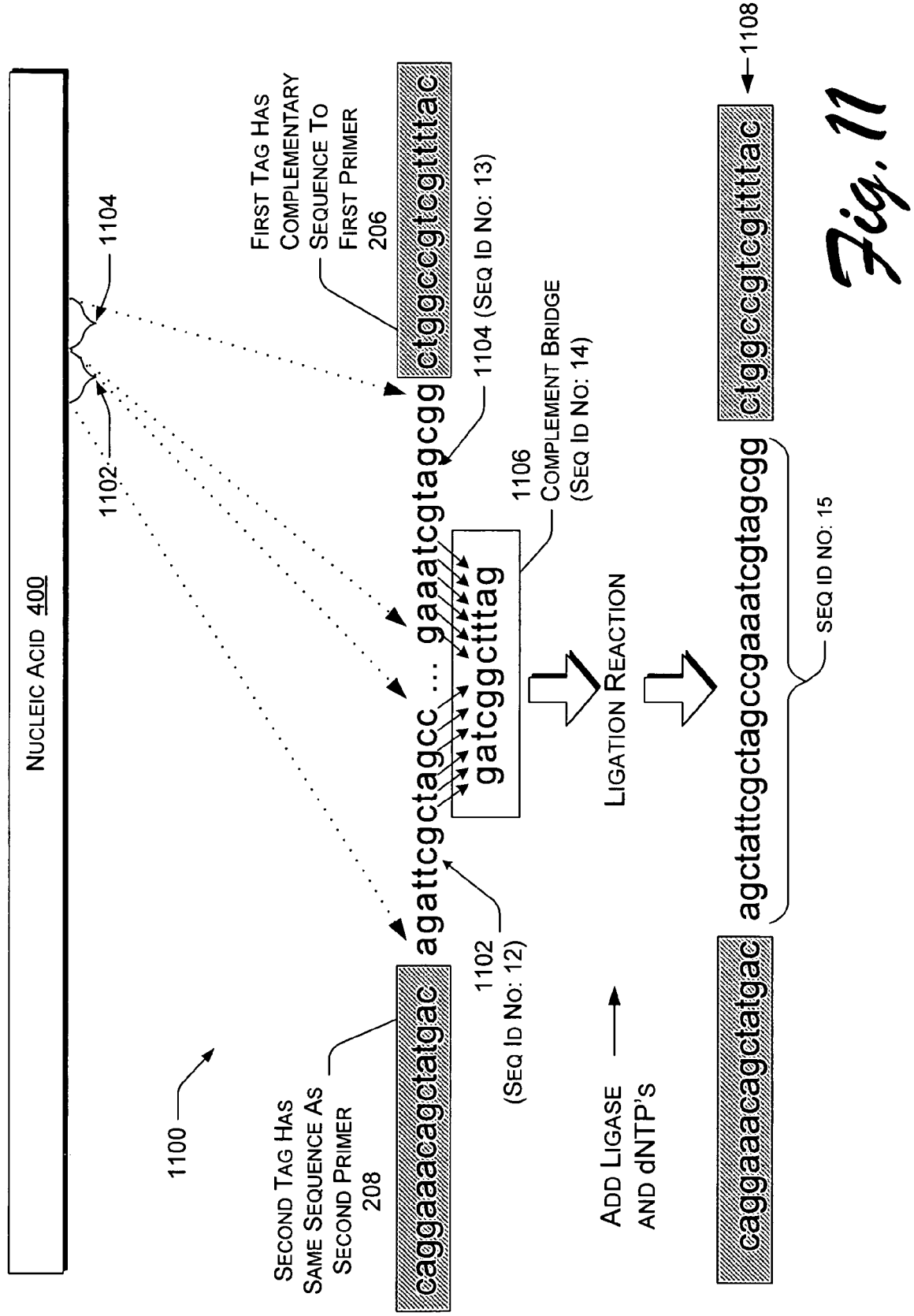
FIG. 11 is a graphic representation of an exemplary method of ligation extension of example tagged reference nucleic acid oligonucleotides SEQ ID NO: 12 and SEQ ID NO: 13 using example bridge sequence SEQ ID NO: 14 to make example reference nucleic acid sequence SEQ ID NO: 15.

FIG. 11 shows an exemplary ligation extension method 1100 that can be used alone or in addition to other exemplary techniques described herein. The exemplary method 1100 can join two oligonucleotides, allowing a reference nucleic acid architect to design and synthesize smaller, simpler oligonucleotides to be joined into longer, more complex oligo- or polynucleotides later on in the design, synthesis, amplification cycle—before (or in some cases after) amplification. The exemplary method 1100 provides another tool for designing, synthesizing, and/or propagating reference nucleic acids, in this case a tool for facilitating rapid synthesis of longer nucleic acid base sequences for use as references in molecular diagnostic and genetic testing of human or nonhuman nucleic acid base sequences. In other words, the exemplary method 1100 allows a larger reference nucleic acid to be built from smaller, more manageable, and more manipulable pieces.

In one implementation, the exemplary method 1100 uses exemplary ligation extension components and reaction parameters, such as those indicated in Appendix B: "Synthetic Control Design Parameters: Exemplary Ligation Extension Components and Reaction Parameters," incorporated herein by reference.

An exemplary method 1100 can be used for joining two of any amenable types of oligonucleotides, but is especially useful for joining synthetic oligonucleotides e.g., 1102 SEQ ID NO: 12 and 1104 SEQ ID NO: 13 that represent adjacent segments of a genomic nucleic acid 400, wherein the adjacent segments modeled by the synthetic oligonucleotides 1102 SEQ ID NO: 12 and 1104 SEQ ID NO: 13 are both relevant as clinical references. Alternatively, it may be desirable to join two reference nucleic acids for physical, chemical, steric, and/or practical reasons related to supply and packaging logistics of a particular reference nucleic acid mixture 718.

Each oligonucleotide to be ligated (e.g., 1102 SEQ ID NO: 12 and 1104 SEQ ID NO: 13) is synthesized with an exemplary tag (e.g., 206 SEQ ID NO: 2 and 208 SEQ ID NO: 5) on the end opposite of its candidate ligation site. An additional oligonucleotide comprising a complement bridge sequence 1106 SEQ ID NO: 14 is introduced accompanied by ligase (a ligation enzyme) and dNTPs (the individual base unit "monomers" to become the building blocks for strand extension). One end of the complement bridge sequence 1106 SEQ ID NO: 14 has a base sequence complementary to the non-primer-tag end of one of the oligonucleotides 1102 SEQ ID NO: 12 to be ligated and the other end of the complement bridge sequence 1106 SEQ ID NO: 14 has a base sequence complementary to the non-primer-tag end of the other oligonucleotide 1104 SEQ ID NO: 13 to be ligated. The tagged reference oligonucleotides—1102 bound to 208 (SEQ ID NO: 12 plus SEQ ID NO: 5) and 1104 bound to 206 (SEQ ID NO: 13 plus SEQ ID NO: 2) align by complementation onto the complement bridge sequence 1106 SEQ ID NO: 14 that acts as template and "bridge." The ligase joins the two or more oligonucleotides (e.g., 1102 SEQ ID NO: 12 and 1104 SEQ ID NO: 13), creating a single oligonucleotide 1108 (SEQ ID NO: 15 plus SEQ ID NO: 2 plus SEQ ID NO: 5) from the two original oligonucleotides 1102 SEQ ID NO: 12 and 1104 SEQ ID NO: 13.

Once the single oligonucleotide 1108 is created from the two original oligonucleotides 1102, 1104, the single oligonucleotide 1108 may be amplified singly or in an exemplary mixture 601 by an exemplary method such as those depicted with regard to FIGS. 5 and 6.

Figure 12:
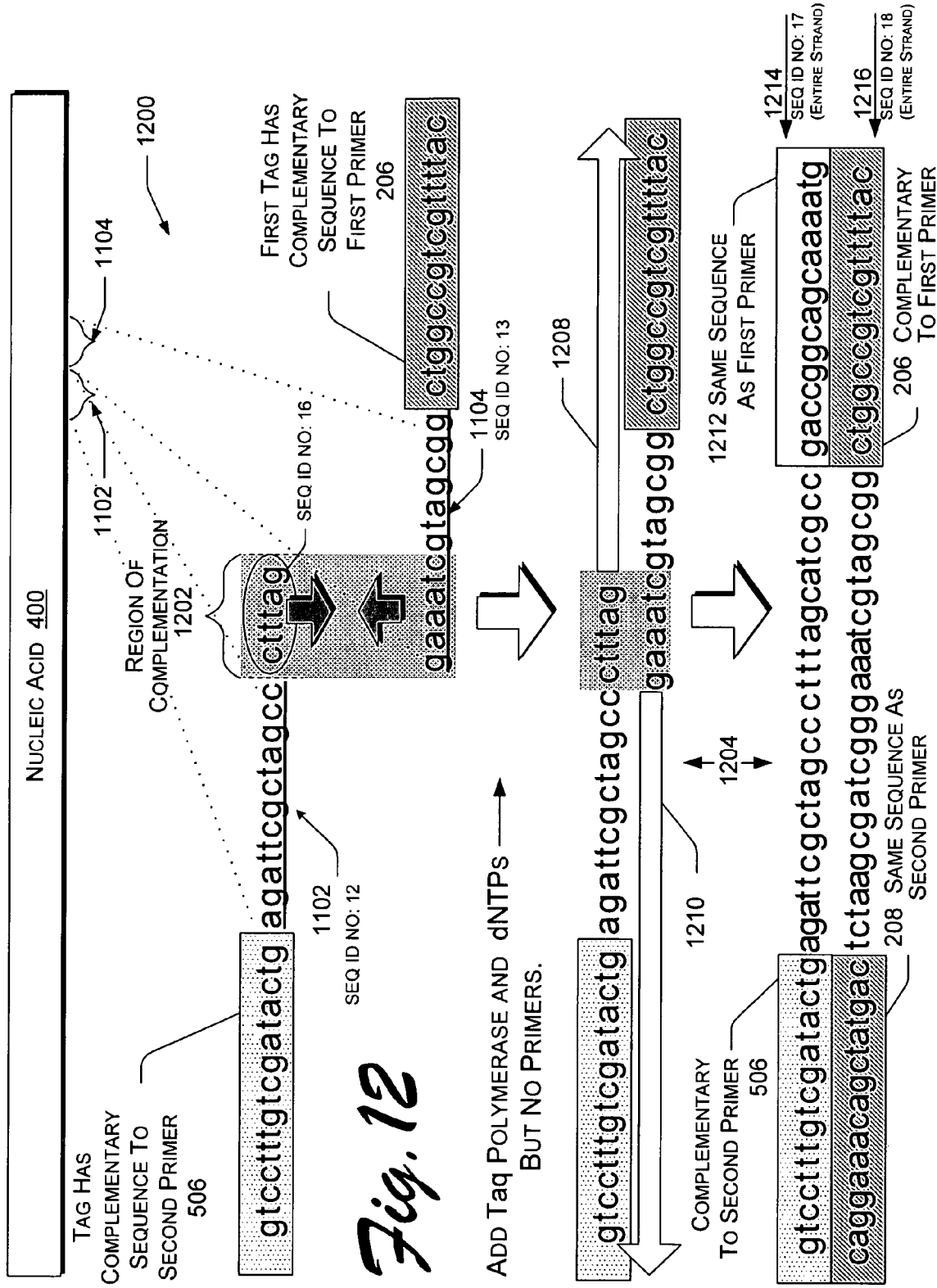
FIG. 12 is a graphic representation of an exemplary method of overlap extension of example reference nucleic acid oligonucleotides SEQ ID NO: 12 and SEQ ID NO: 13 by synthesizing an example region of complementation SEQ ID NO: 16 in order to make example longer polynucleotides SEQ ID NO: 17 and SEQ ID NO: 18.

FIG. 12 shows an exemplary overlap extension method 1200 that can be used alone or in addition to other exemplary techniques described herein. The exemplary method 1200 can join two or more oligonucleotides 1102 SEQ ID NO: 12 and 1104 SEQ ID NO: 13 on either side of a region of complementation 1202, allowing (in a manner similar to the exemplary method 1100 above) the reference nucleic acid architect to design and synthesize smaller, simpler oligonucleotides to be joined into longer, more complex oligonucleotides or polynucleotides later on in the design, synthesis, amplification cycle—i.e., before (or in some cases after) amplification. The exemplary method 1200 provides another member in a toolbox of exemplary techniques for designing, synthesizing, and/or propagating reference nucleic acids for use as references in molecular diagnostic and genetic testing of human or nonhuman nucleic acid base sequences. The exemplary method 1200 allows a larger reference nucleic acid to be built from smaller, more manageable, and more manipulable pieces.

In one implementation, the exemplary method 1200 uses exemplary overlap extension components and reaction parameters, such as those indicated in Appendix C: "Synthetic Control Design Parameters: Exemplary Overlap Extension Components and Reaction Parameters," incorporated herein by reference.

In the exemplary overlap extension method 1200, a region of complementation 1202 is designed into the base sequence of one or both of the oligonucleotides 1102, 1104 to be overlapped, except in the unlikely event that both oligonucleotides 1102, 1104 already have complementary ends opposite to their respective tag ends (i.e., the ends bearing tags associated with a primer set for amplification). In the illustrated case, an end sequence SEQ ID NO: 16 is synthesized onto oligonucleotide 1102 SEQ ID NO: 12 to provide complementation with part of oligonucleotide 1104 SEQ ID NO: 13.

So that the duplex 1204 resulting from this exemplary method 1200 may be amplified singly or in an exemplary mixture 601 by an exemplary method such as those depicted with regard to FIGS. 5 and 6, tags (e.g., 206 SEQ ID NO: 2 and 506 SEQ ID NO: 8) for use with a primer set (e.g., 402) are designed and synthesized onto the not-to-be-overlapped ends of each of the reference oligonucleotides 1102, 1104, that is, on the ends opposite to the respective regions of complementation 1202.

In one implementation, the tags (e.g., 206 SEQ ID NO: 2 and 506 SEQ ID NO: 8) for both reference oligonucleotides 1102, 1104 are complementary to their respective primers (e.g., 404 SEQ ID NO: 4 and 406 SEQ ID NO: 5). It should be noted that multiple reference oligonucleotides can intervene and be incorporated by exemplary ligation techniques between the end reference nucleotides 1102 and 1104 bearing the exemplary tags complementary to the primers, as will be discussed with respect to FIG. 13. When the oligonucleotides 1102, 1104 bound to their corresponding regions of complementation 1202 and to their tags 205, 506 are placed together with Taq polymerase and dNTPs, but no primers for PCR, the corresponding one or more regions of complementation 1202 anneal to each other and each act as a primer for extending the two or more overlapped stands (1102 bound to both 506 and 1202, overlapping 1104 bound to 206) in opposite directions (1208, 1210) into a duplex 1204 longer than either of the overlapped strands, consisting of example longer polynucleotide strands 1214 SEQ ID NO: 17 and 1216 SEQ ID NO: 18.

Each end strand (i.e., bearing a tag) of the duplex 1204 receives a respective end base sequence 1212 SEQ ID NO: 4 and 208 SEQ ID NO: 5 that matches the base sequence of respective members of the primer set 402 (sequences 404 SEQ ID NO: 4 and 406 SEQ ID NO: 5). Each end strand already includes a tag (206 SEQ ID NO: 2 and 506 SEQ ID NO: 8) complementary to the remaining member of the primer set 402 (sequences 404 SEQ ID NO: 4 and 406 SEQ ID NO: 5). Hence, each end strand of the resulting duplex 1204 includes the correct tags for being amplified singly or in an exemplary mixture 601 by an exemplary method such as those described with regard to FIGS. 5 and 6 and can enter into those exemplary methods 500, 600 using a denaturation step to separate the strands.

Figure 13:
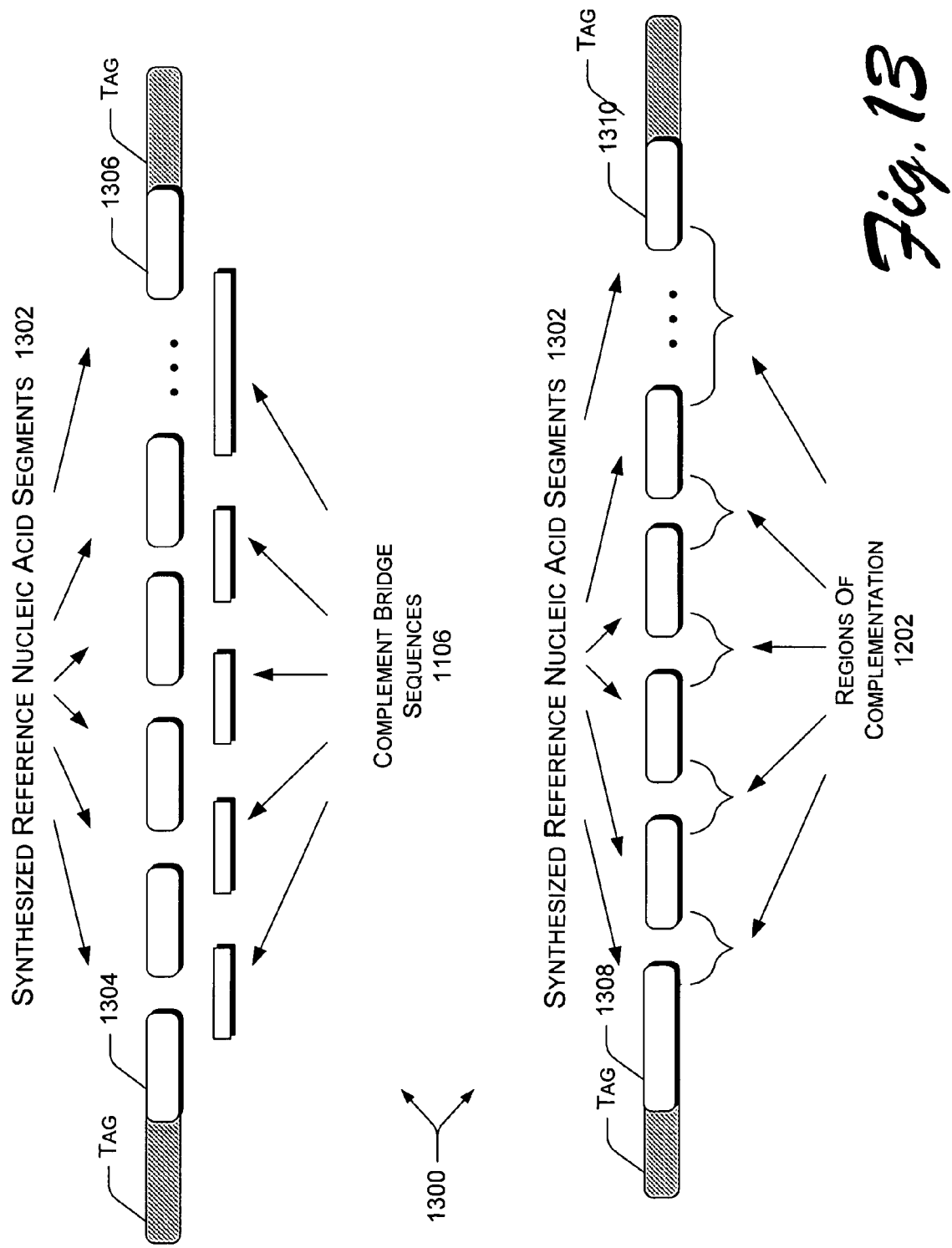
FIG. 13 is a graphic representation of exemplary ligation methods for multiple segments of reference nucleic acid.

FIG. 13 shows exemplary ligation methods 1300 in which multiple complement bridge sequences 1106 (not necessarily identical) and/or multiple regions of complementation 1202 (not necessarily identical) are used to ligate multiple synthesized reference nucleic acid segments 1302. Thus, a single reference nucleic acid may be synthesized by ligating the multiple segments 1302, by exemplary methods described with respect to FIGS. 11 and/or 12, wherein end sequences 1304, 1306; 1308, 1310 bear exemplary tags.

Figure 14:
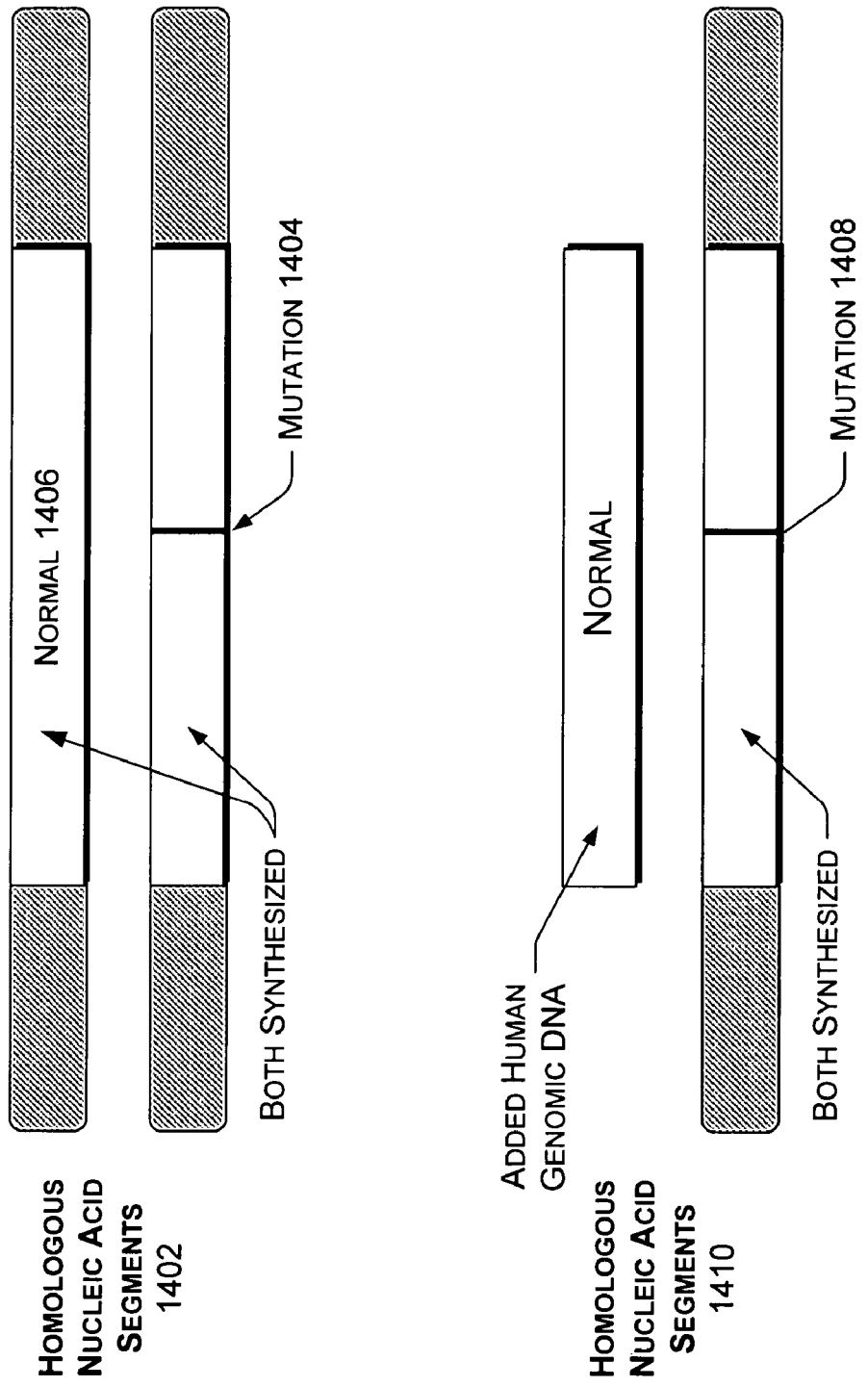
FIG. 14 is a graphic representation of exemplary methods for making synthetic and semi-synthetic homologous gene segments and alleles for carrier testing.

FIG. 14 shows an exemplary method 1400 of designing, synthesizing, and/or propagating one or more reference nucleic acids for carrier testing: to simulate at least part of the genetic profile of a heterozygous carrier. The resulting reference nucleic acid or mixture of reference nucleic acids may be synthetic or semi-synthetic.

In one implementation, a mixture of different pairs of homologous nucleic acid segments 1402 (one pair illustrated) are designed, synthesized, and propagated using one or more of the exemplary methods described herein. That is to say, for at least some pieces of reference nucleic acid designed and synthesized with one or more mutations 1404 by an exemplary method, homologous pieces of nucleic acid 1406 without the one or more mutations are also designed and synthesized. This implementation of the exemplary method 1400 can produce a mixture of reference nucleic acids that is heterozygous at particular loci wherein a mutation occurs in only one member of the homologous pair, e.g., in only one of the alleles of a homologous gene pair. This simulates the heterozygous makeup of a heterozygous carrier.

In another implementation of an exemplary method 1400, homozygotes that include one or more mutations 1408 are designed and synthesized by one or more of the exemplary methods described herein. Normal human genomic DNA (or other normal human or animal or plant of other organism nucleic acid) is added to the mixture, thereby forming heterozygous loci wherever there is a piece of homologous reference nucleic acid bearing a mutation. Such an exemplary mixture of synthetic elements and human biological elements simulates homologous gene pairs that are heterozygous at every locus of interest—in other words, the exemplary mixture provides carrier testing across many different loci.

To reiterate, in one implementation, an exemplary mixture of synthesized multiple reference nucleic acids for carrier testing is designed and synthesized using exemplary tags tuned to primer sets as described herein, and the exemplary mixture also contains partial or total genomic DNA from a reference human source that is known to differ at least one locus from one or more of the synthesized multiple reference nucleic acids.

Exemplary Systems

Figure 15:
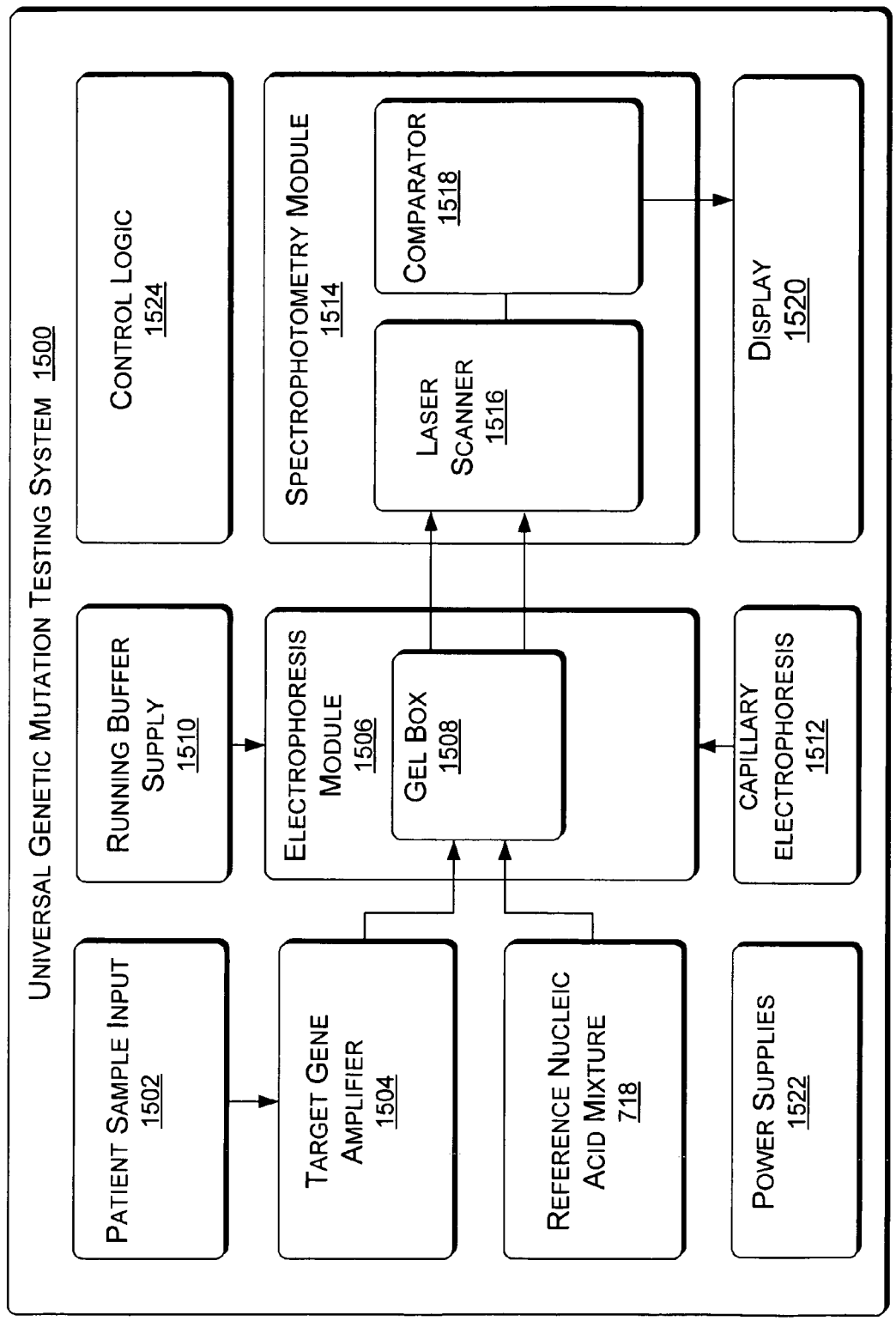
FIG. 15 is a block diagram of an exemplary universal genetic mutation testing system.

FIG. 15 shows an exemplary universal genetic mutation testing system (UGMTS) 1500. Such an exemplary UGMTS 1500 includes hardware, software, lab ware, chemical processors, chemical reagents, control logic, etc., compatible with using an exemplary reference nucleic acid mixture 718 produced as described herein as a universal reference or control, wherein the universe of tests for which the reference nucleic acid mixture 718 is "universal" typically includes a battery of genetic mutation tests associated with a certain gene or a particular disease.

In one implementation, the reference nucleic acid mixture 718 includes multiple constituent reference nucleic acids that are normal manifestations of patient gene sites being tested, and therefore the reference nucleic acid mixture 718 is compared directly with the patient's nucleic acids. In another implementation, the reference nucleic acid mixture 718 includes multiple constituent reference nucleic acids that are manifestations of mutated gene sites being tested, and therefore the reference nucleic acid mixture 718 is used to calibrate and/or verify a set of normal gene controls, which are being compared directly with the patient's nucleic acid, or to calibrate and/or verify the operation of the apparatus (1500) itself.

In an example configuration of the former implementation, an exemplary reference nucleic acid mixture 718 has been designed, synthesized, and amplified so that it contains constituent reference nucleic acids that may be compared directly with amplified samples of a patient's nucleic acid in order to perform a battery of tests for different genetic mutations that could be causing the same disease. Accordingly, an exemplary UGMTS 1500 includes a patient sample input 1502 coupled with a target gene amplifier 1504. The target gene amplifier 1504 may be a PCR apparatus or PCR process to produce a large enough quantity of a patient's target gene (gene of interest) to perform a battery of mutation tests.

The reference nucleic acid mixture 718 and the patient's nucleic acid from the target gene amplifier 1504 are both fed to an electrophoresis module 1506 that includes a gel box 1508 for simultaneous gel electrophoresis of the patient's nucleic acid and the reference nucleic acid mixture 718. The gel box 1508 is supported by a running buffer supply 1510 and a capillary electrophoresis module 1512. A spectrophotometry module 1514 coupled with the electrophoresis module 1506 includes a laser scanner 1516 to read the results of the gel electrophoresis. A comparator 1518 evaluates readings obtained by the laser scanner 1516 for presentation on a display 1520. The described UGMTS 1500 is supported by appropriate power supplies 1522 and control logic 1524.

The exemplary UGMTS 1500 described above is only one example system that compatibly uses an exemplary reference nucleic acid mixture 718 produced according to the subject matter. Other exemplary systems that include different parts and/or other configurations can also use an exemplary reference nucleic acid mixture 718.

CONCLUSION

The foregoing describes exemplary reference nucleic acids, mixtures of reference nucleic acids, methods of designing, synthesizing, and propagating each, and an exemplary system for using a reference nucleic acid mixture. The description is not meant to be limiting but illustrative of the subject matter.

The invention claimed is:

1. A method of creating a clinical reference solution that models clinically relevant sites on genes responsible for human genetic conditions, wherein the clinical reference solution is substantially free of clinically irrelevant nucleic acid, comprising:
for each clinically relevant site, designing an oligonucleotide comprising an arrangement of bases to model the clinically relevant site as isolated from clinically irrelevant nucleic acid that occurs adjacent to the corresponding clinically relevant site in vivo, including designing two ends of the arrangement to form primer targets for differentially amplifying the modeled clinically relevant site;
for each arrangement, performing a synthesis that includes constructing base-by-base, from end to end, a single strand of bases comprising the arrangement of bases that models the clinically relevant site and forms the primer targets associated with the clinically relevant site; and
mixing each single strand into a single solution to form a collection of oligonucleotides, each representing a clinically relevant site of a gene.

2. The method as recited in claim 1, wherein each clinically relevant site comprises a mutation of a normal human nucleic acid sequence, each mutation representing a human genetic condition.

3. The method as recited in claim 1, wherein:
the synthesizing the single strand includes constructing a first sequence of nucleotides attached base-by-base to a first end of the arrangements of bases, wherein the first sequence is complementary to a nucleotide sequence of a first primer of a primer set, and
the synthesizing the single strand includes constructing a second sequence of nucleotides attached base-by-base to a second end of the arrangements of bases, wherein the second sequence is identical to a nucleotide sequence of a second primer of a primer set.

4. The method as recited in claim 1, wherein the synthesizing comprises constructing, base-by-base, two complementary strands, wherein:
a first strand includes one of the clinically relevant sites and a nucleic acid tag complementary to a first primer of a primer set; and
a second strand is complementary to the first strand and to a nucleic acid tag complementary to a second primer of the primer set.

5. The method as recited in claim 1, wherein:
each modeled clinically relevant site has an associated primer set, and wherein:
the reference solution is tuned for a specific battery of clinical tests by differentially amplifying the different modeled clinically relevant sites to different concentrations in the reference solution.

6. The method as recited in claim 5, wherein different groups of the modeled clinically relevant sites in the reference solution have associated primer sets such that each different group of modeled clinically relevant sites is amplified independently.

7. The method as recited in claim 6, wherein independently amplifying each of the groups of modeled clinically relevant sites includes controlling a physical characteristic of the reference solution to favor an amplification capability of one primer set over an amplification capability of another primer set.

8. The method as recited in claim 1, further comprising adding normal human nucleic acid to the collection of oligonucleotides in order to achieve a mixture of the nucleic acids in the reference solution representing at least a segment of homologous heterozygous alleles.

9. The method as recited in claim 1, further comprising joining two parts of one of the arrangements of bases together using a ligation extension to perform the synthesizing of a large arrangement of bases.

10. The method as recited in claim 9, further comprising using a bridge nucleic acid to join multiple parts of the arrangement of bases.

11. The method as recited in claim 1, further comprising using an overlap extension to join multiple parts of the arrangement of bases.

12. A method for tuning concentrations of different reference nucleic acids within a clinical reference solution, comprising:
designing multiple reference nucleic acids, wherein each reference nucleic acid comprises an arrangement of bases modeling a clinically relevant site on genes responsible for human genetic conditions exclusive of clinically irrelevant human nucleic adjacent to the clinically relevant site in vivo;
for each reference nucleic acid in a first subset of the multiple reference nucleic acids, constructing an oligonucleotide comprising an arrangement of bases to model the clinically relevant site as isolated from clinically irrelevant nucleic acid that occurs adjacent to the corresponding clinically relevant site in vivo, including designing two ends of the arrangement to form a first pair of primer targets allowing PCR amplification of the first subset via a primer set specific to the first pair of primer targets;
for each reference nucleic acid in a second subset of the multiple reference nucleic acids, constructing an oligonucleotide comprising an arrangement of bases to model the clinically relevant site as isolated from clinically irrelevant nucleic acid that occurs adjacent to the corresponding clinically relevant site in vivo, including designing two ends of the arrangement to form a second pair of primer targets allowing PCR amplification of the second subset via a second primer set specific to the second pair of primer targets; and
wherein each oligonucleotide in the first and second subsets is constructed base-by-base, from end to end, as a single strand.

13. The method as recited in claim 12, further comprising combining the first and second subsets to make a single mixture and differentially amplifying the first subset and the second subset in a PCR reaction by controlling amounts of the first primer set and the second primer set in the single mixture.

14. The method as recited in claim 13, further comprising adding normal human nucleic acid to the single mixture to obtain heterozygous pairs, wherein each heterozygous pair includes a normal segment of human nucleic acid and a mutated copy of the normal segment of human nucleic acid.

15. The method as recited in claim 1, further comprising differentially amplifying each different type of oligonucleotide in the single solution to a respective clinically relevant concentration.

16. The method as recited in claim 15, wherein the amplifying increases the number of each single strand exponentially.

17. The method as recited in claim 15, wherein each single strand creates its own complementary single strand during the amplifying.

* * * * *